(12) United States Patent
Chae et al.

(10) Patent No.: US 8,815,263 B2
(45) Date of Patent: Aug. 26, 2014

(54) TANDEM FACIAL AMPHIPHILES

(71) Applicant: Wisconsin Alumni Research Foundation, Madison, WI (US)

(72) Inventors: Pil Seok Chae, Ansan (KR); Samuel Helmer Gellman, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/669,198

(22) Filed: Nov. 5, 2012

(65) Prior Publication Data

US 2013/0115251 A1    May 9, 2013

Related U.S. Application Data

(60) Provisional application No. 61/556,625, filed on Nov. 7, 2011.

(51) Int. Cl.
*A61K 9/00* (2006.01)
*C07K 1/00* (2006.01)
*A23J 1/00* (2006.01)
*C07J 41/00* (2006.01)

(52) U.S. Cl.
USPC ............ 424/400; 530/350; 530/422; 536/5

(58) Field of Classification Search
CPC ..... A61K 47/28; A61K 47/26; A61K 9/1075; C07J 41/0061
See application file for complete search history.

(56) References Cited

PUBLICATIONS

Chae et al., "Tandem Facial Amphiphiles for Membrane Protein Stabilization," JACS Communications (2010) 132 (47): 16750-16752.

Chae et al., "Maltose-neopentyl glycol (MNG) amphiphiles for solubilization, stabilization and crystallization of membrane proteins," Nature America, Inc. (2010) 7 (12): 1003-1008.
Cheng et al., "Facial Amphiphiles," J. Am. Chem. Soc. (1992) 114 (18): 7319-7320.
Hjelmeland, "The Design and Synthesis of Detergents for Membrane Biochemistry," Methods in Enzymology (1986) 124: 135-164.
Hovers et al., "A class of mild surfactants that keep integral membrane proteins water-soluble for functional studies and crystallization," Molecular Membrane Biology (2011) 28 (3): 171-181.
McGregor et al., "Lipopeptide detergents designed for the structural study of membrane proteins," Nature Publishing Group (2003) 21: 171-176.
Rosenbaum et al., "Structure and function of an irreversible agonist-β2 adrenoceptor complex," Nature (2011) 469: 236-240.
Rasmussen et al., "Structure of a nanobody-stabilized active state of the β2 adrenoceptor," Nature (2011) 469: 175-180.
Schafmeister et al., "Structure at 2.5 A of a Designed Peptide That Maintains Solubility of Membrane Proteins," Science (1993) 262: 734-738.
Zhang et al., "Designing Facial Amphiphiles for the Stabilization of Integral Membrane Proteins**," Wiley-VCH Verlag GmbH & Co. (2007) 46: 7023-7025.

*Primary Examiner* — Michael G Hartley
*Assistant Examiner* — Sun Y Kim
(74) *Attorney, Agent, or Firm* — Joseph T. Leone, Esq.; Daniel A. Blasiole; DeWitt Ross & Stevens SC

(57) ABSTRACT

The invention provides tandem facial amphiphiles for biochemical manipulations and characterization of membrane proteins, such as intrinsic membrane proteins. Members of this new family display favorable behavior with several membrane proteins. These amphiphiles can form relatively small micelles, and small changes in amphiphile chemical structures can result in large changes in their physical properties. The tandem facial amphiphiles can be used to aid the solubilization, isolation, purification, stabilization, crystallization, and/or structural determination of membrane proteins.

20 Claims, 11 Drawing Sheets

TANDEM FACIAL AMPHIPHILES

RELATED APPLICATIONS

This application claims priority under 35 U.S.C. §119(e) to U.S. Provisional Patent Application No. 61/556,625, filed Nov. 7, 2011, which is incorporated herein by reference.

GOVERNMENT SUPPORT

This invention was made with government support under GM075913 awarded by the National Institutes of Health. The government has certain rights in the invention.

BACKGROUND OF THE INVENTION

Membrane proteins (MPs) play crucial roles in biology, but these proteins are difficult to handle and analyze because of their physical properties. The native conformations of MPs display extensive nonpolar surfaces. The display of these nonpolar surfaces is necessary for residence in a lipid bilayer but leads to denaturation and/or aggregation in an aqueous medium. Detergents such as dodecyl-β-D-maltoside (DDM) are typically employed to render MPs soluble by coating the nonpolar protein surfaces. However, only some MPs can be maintained in native-like conformations when solubilized with conventional detergents (Serrano-Vega et al., *Proc. Natl. Acad. Sci. USA* 2008, 105, 877-882). Moreover, even when a native conformation can be achieved, the MP-detergent complex may manifest unfavorable properties with regard to structural analysis, such as the inability to crystallize and/or the formation of complexes too large for NMR analysis. Because our understanding of membrane protein structure and function remains poorly developed relative to soluble proteins, there is a persistent need for new amphiphilic "assistants" that can promote solubilization and manipulation of MPs.

Several groups have reported creative implementations of the "facial amphiphile" concept for the design of novel amphiphiles that display favorable behavior with selected membrane proteins (see for example, Cheng et al., *J. Am. Chem. Soc.* 1992, 114, 7319-7320; Schafmeister et al., *Science* 1993, 262, 743-738). For example, McGregor et al. reported lipopeptides that are intended to match the width of a lipid bilayer and form a sheath around nonpolar surfaces of MPs (*Nat. Biotech.* 2003, 21, 171-176). Zhang et al. have developed cholate-based amphiphiles in which hydrophilic maltose units project from one side of the rigid and hydrophobic steroidal skeleton (*Angew. Chem. Int. Ed.* 2007, 119, 7153-7155). While these approaches promote the solubilization and aid the manipulation of some MPs, they are not universally effective for all MPs.

Accordingly, there is a need for new amphiphiles for the solubilization of MPs. There is also a need for new amphiphiles that aid the isolation and manipulation of MPs, such as amphiphiles that approximate the width of a lipid bilayer to form a sheath around nonpolar surfaces of MPs, and amphiphiles that can help to maintain the MPs in native-like conformations when solubilized.

SUMMARY

The invention provides tandem facial amphiphiles for membrane protein manipulation. The manipulation can include solubilization, stabilization, isolation, purification, crystallization and/or structural determination. A tandem facial amphiphile can be a compound of Formula I:

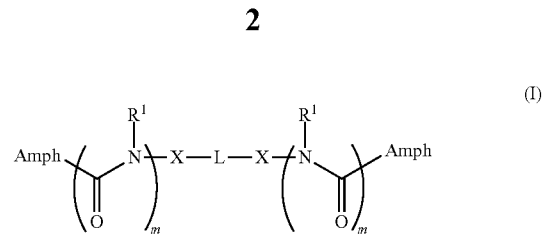

where L is —$(CH_2)_n$— where n is 1-10; $(C_5-C_8)$cycloalkyl; a phenyl diradical optionally substituted by 1, 2, 3, or 4 $(C_1-C_4)$alkyl groups; —$C(R^x)_2$—; or —$CH_2$—$C(R^x)_2$—$CH_2$—; where each $R^x$ is independently H, OH, or —$CH_2$O-Sac;

each X is independently O, S, NH, $CH_2$, triazole, or a direct bond;

each m is 0 or 1;

each $R^1$ is independently H or $(C_1-C_{20})$alkyl; and each Amph is independently a moiety of Formula A:

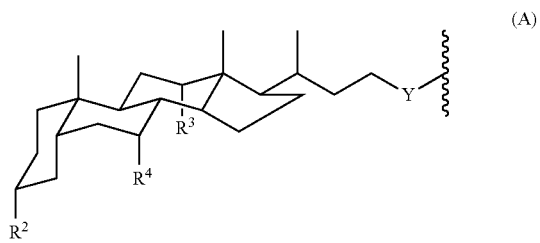

wherein

Y is $CH_2$ or a direct bond;

each $R^2$, $R^3$, and $R^4$ is independently H, OH, or O-Sac; and each Sac is independently an oxygen-linked monosaccharide, disaccharide, or trisaccharide where the compound of Formula I has at least 4 Sac groups. In some embodiments, the compound has 4, 5, 6, 7, or 8 Sac groups.

In some embodiments, the compound is a compound of Formula II:

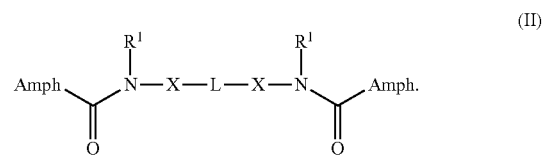

In some embodiments, the compound is a compound of Formula III:

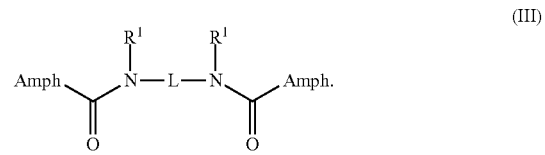

In some embodiments, the compound is a compound of Formula IV:

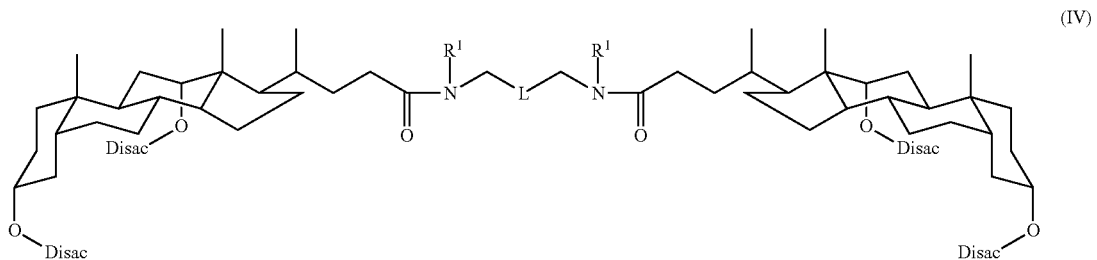

where each $R^1$ is independently $(C_1$-$C_{20})$alkyl, L is not $CH_2$, and each Disac is independently a disaccharide moiety, such as a maltosyl group. In some embodiments, $R^1$ is $CH_3$; $CH_2CH_3$; $CH_2(CH_3)_2$; $(CH_2)_3CH_3$; or $(CH_2)_4CH_3$.

In some embodiments, the compound is a compound of Formula V:

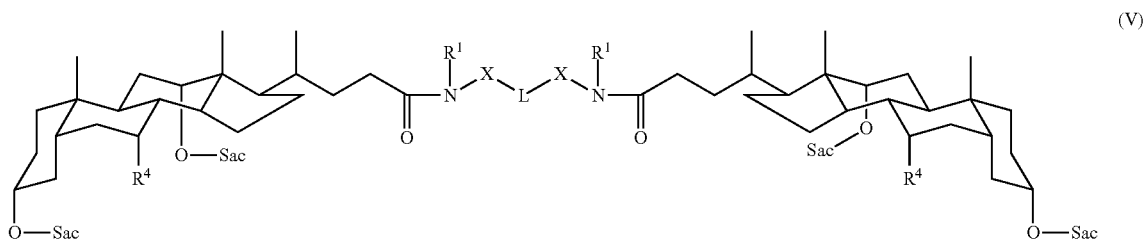

where Sac and $R^4$ are as defined for Formula A.

In some embodiments, the compound is a compound of Formula VI:

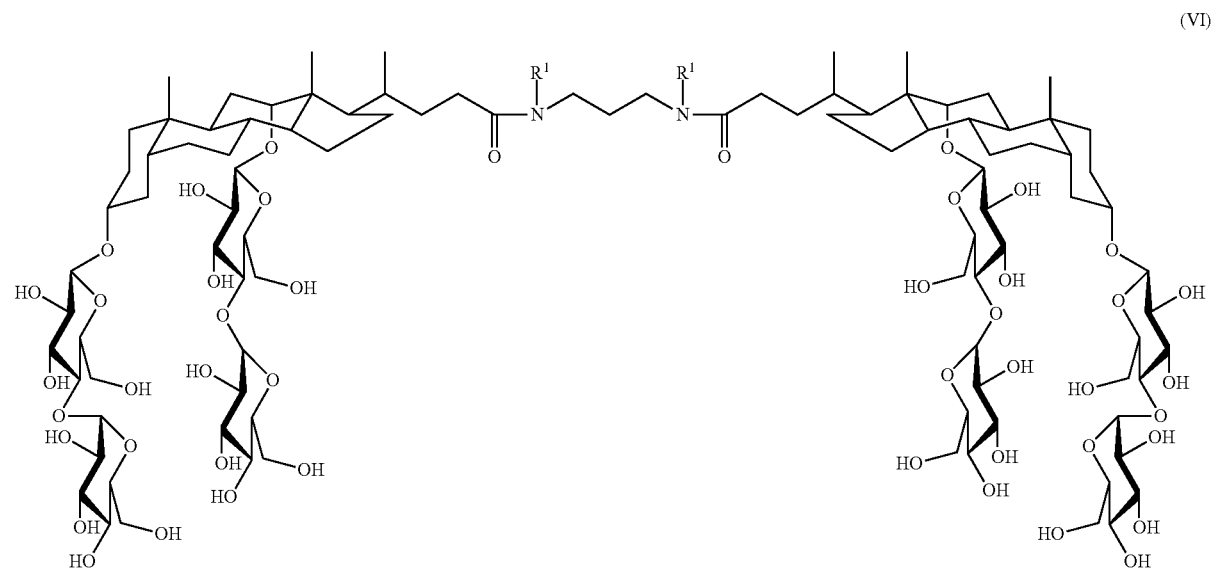

where $R^1$ is as defined herein.

In some embodiments, the compound is a compound of Formula I wherein m is 0 and Y is $CH_2$, for example, a compound of Formula VII:

(VII)
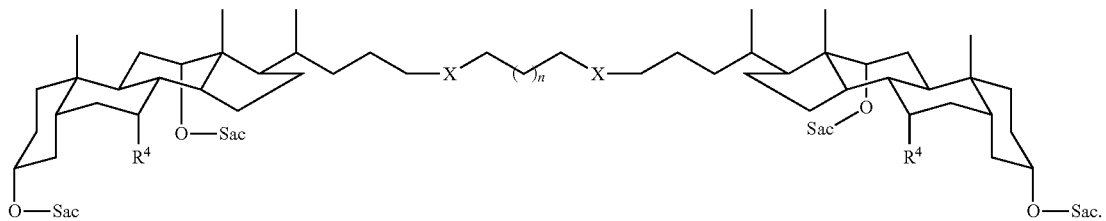
In Formula VII, each X can be independently, for example, O, S, NH, CH$_2$, or triazole; and n can be −1, 0, 1, 2, 3, 4, 5, 6, 7, 8, 9, or 10. Accordingly, when n is −1, only one methylene group is present between the two X groups.
In some embodiments, the compound is a compound of Formula VIII:
(VIII)
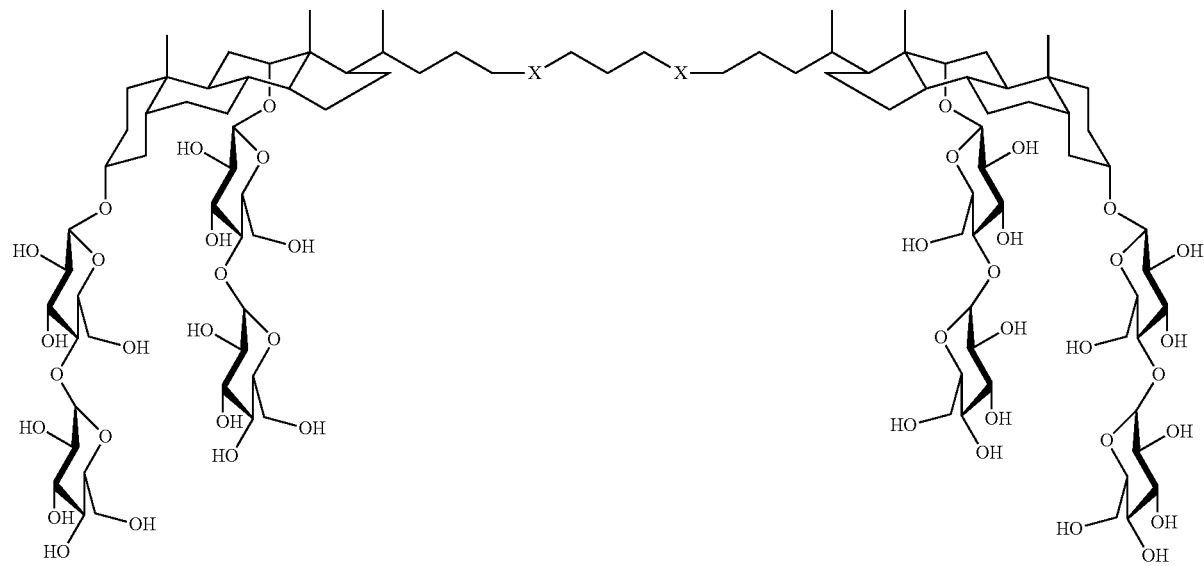
wherein each X is S, O, CH$_2$, or triazole, for example,
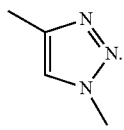
In some embodiments, the compound is a compound of Formula IX:
(IX)
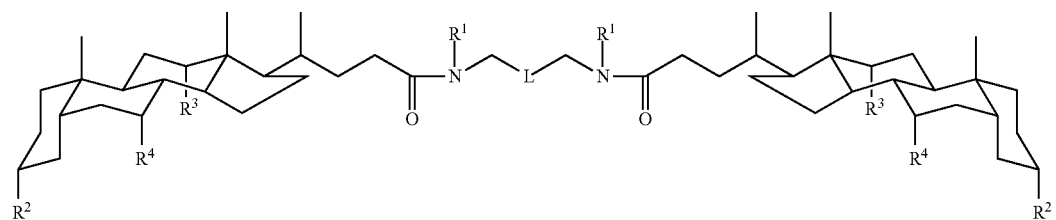

where each $R^2$ is independently an oxygen-linked monosaccharide, disaccharide, trisaccharide. Specific examples of $R^2$ include, but are not limited to, —O-glucosyl, —O-maltosyl, —O-galactosyl, and the like.

In some embodiments, the compound is a compound of Formula X:

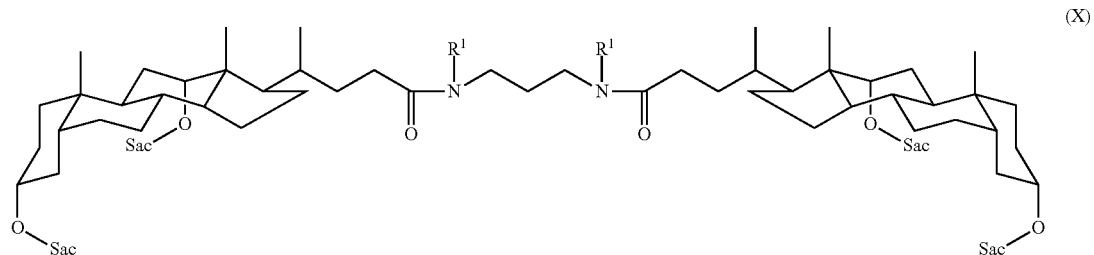

(X)

where Sac and $R^1$ are as defined for Formula I. In some embodiments, each Sac is a monosaccharide or a disaccharide.

In some embodiments, the compound is a compound of Formula XI:

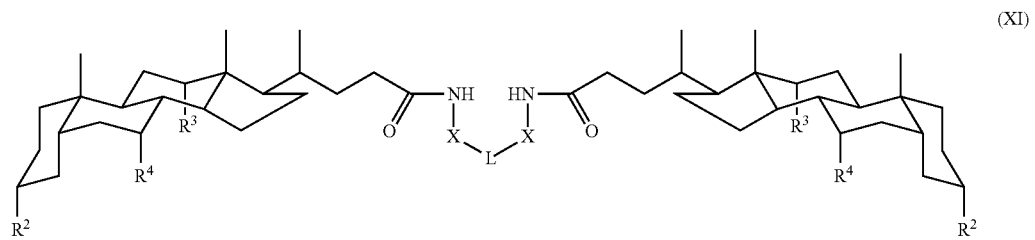

(XI)

where each variable is as defined for Formula I.

In some embodiments, the compound is a compound of Formula XII:

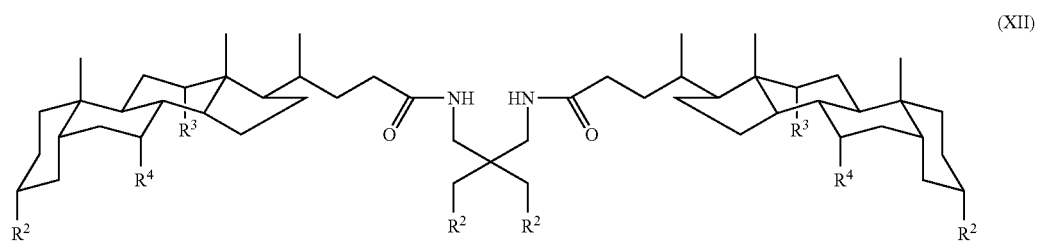

(XII)

where each $R^2$ is independently an oxygen linked monosaccharide, disaccharide, trisaccharide, and $R^3$ and $R^4$ are as defined for Formula I.

In some embodiments, the compound is a compound of Formula XIII:

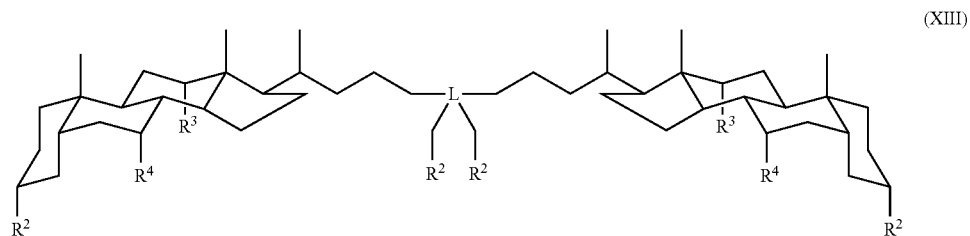

(XIII)

wherein L is a quaternary carbon and R², R³ and R⁴ are as defined for Formula I.

In some embodiments, the compound is a compound of Formula:

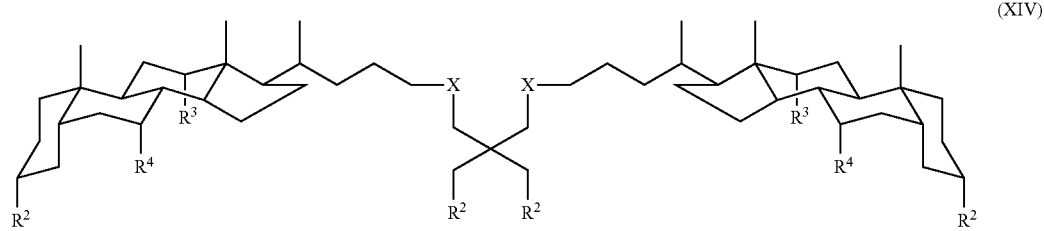

(XIV)

where each R² is independently a monosaccharide, disaccharide, trisaccharide, and X, R³ and R⁴ are as defined for Formula I.

In some embodiments, the critical micelle concentration (CMC) of the compound in water is about 4 μM to about 20 μM. The hydrodynamic radii ($R_h$) of micelles of the compound in water can be about 1.8 nm to about 3.4 nm. A plurality of the compounds can form a micelle in water comprising about 6 to about 15 molecules of the compound. Some micelles can include about 5 to about 10, about 10 to about 15, about 5 to about 20, about 5 to about 15, about 10 to about 20, or about 5 to about 25 molecules of the compound in the formation of individual micelles.

The invention also provides a composition comprising a plurality of compounds as described above and an isolated membrane protein. The micelle can optionally include one or more drugs, therapeutic molecules, bioactive molecules, polypeptides, proteins, genes, or a combination thereof, within the micelle. In some embodiments, the molecule within the micelle is a polypeptide or a protein.

The invention also provides methods of solubilizing or stabilizing a membrane protein comprising contacting a membrane protein with an effective amount of a plurality of compounds as described herein, in an aqueous solution, and optionally heating the protein and the compounds, thereby forming a solubilized or stabilized aggregation of the compounds and the membrane protein. The aggregation of the compounds can be in the form of a micelle. The invention further provides methods of extracting a protein from a lipid bilayer comprising contacting the lipid bilayer with an effective amount a plurality of compounds as described herein in an aqueous solution to form a mixture, optionally in the presence of a buffer, thereby forming an aggregation of the compounds and the membrane protein that has been extracted from the lipid bilayer. The aggregation and/or micelles can then be separated from the mixture.

The invention therefore provides novel compounds and formulas, intermediates for the synthesis of the compounds and formulas, as well as methods of preparing the compounds, formulas, and compositions described herein. The invention also provides compounds that are useful as intermediates for the synthesis of other valuable compounds. The invention further provides methods of using the compounds, for example, to aid the solubilization, isolation, purification, stabilization, crystallization, and/or structural determination of membrane proteins. The compounds of the invention can be used alone, or in combination with lipids or known detergents. Other objects, features and advantages of the present invention will become apparent from the following description, claims and drawings.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention, however, one skilled in the art will understand that portions of the example or aspect may be used in combination with other examples or aspects of the invention.

DETAILED DESCRIPTION

Figure 1:
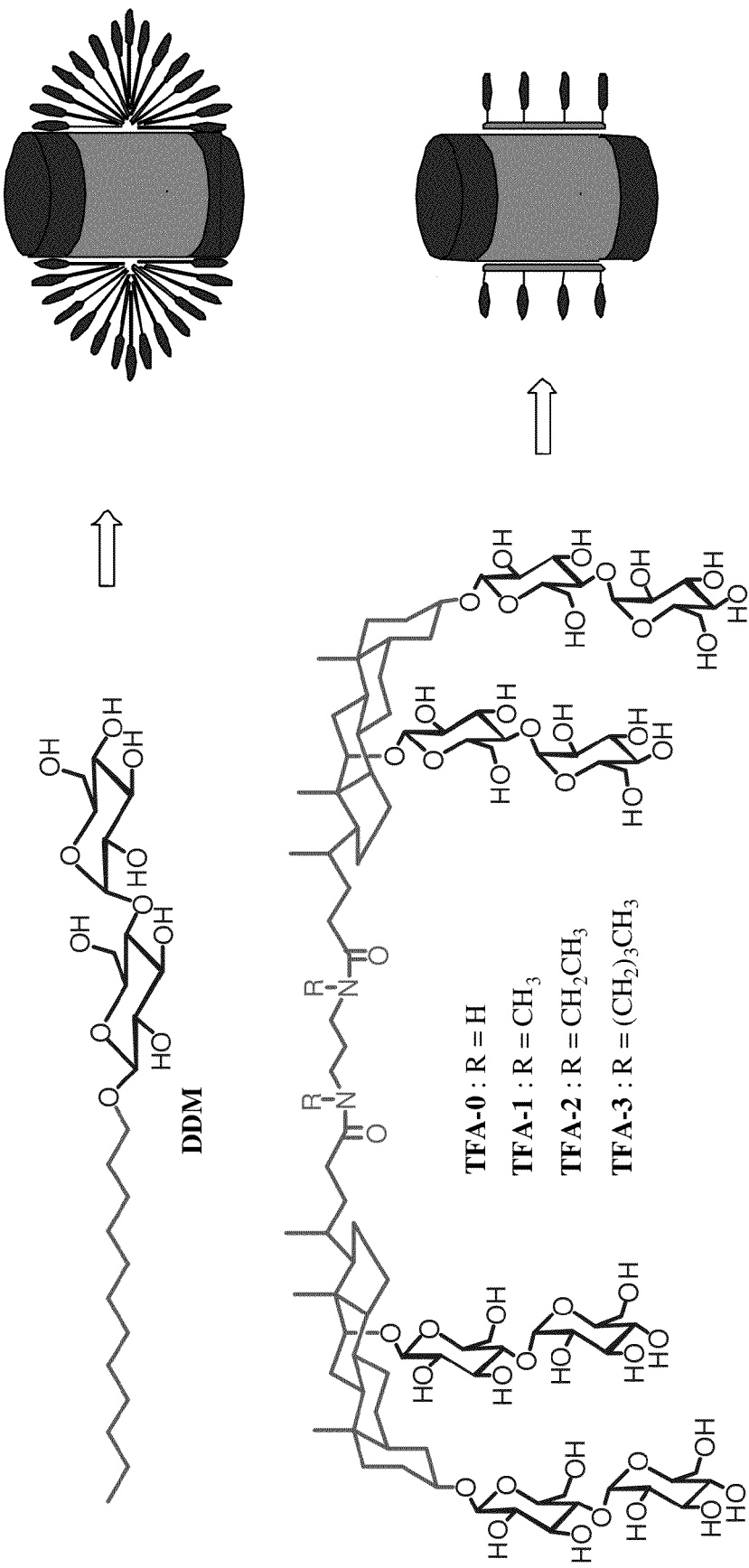
FIG. 1. Chemical structures of DDM (top left), tandem facial amphiphiles (TFAs, bottom left), and schematic representations of membrane proteins interacting with DDM (top right) and TFAs (bottom right).

The invention provides a new family of synthetic amphiphiles, the tandem facial amphiphiles (TFAs), which can be used to support biochemical characterization of membrane proteins, such as the difficult to handle intrinsic membrane proteins. Analyses show that members of this family display favorable behavior with several examples of membrane proteins. Moreover, these amphiphiles form relatively small micelles, a property can be advantageous for manipulating membrane proteins.

The design of TFAs, for example, TFAs that contain a pair of maltose-functionalized deoxycholate units, is described herein. Unlike previous cholate-based designs, the TFAs are long enough to match bilayer width (FIG. 1), and unlike lipopeptides, the TFAs are readily synthesized in large quantities. One TFA forms micelles containing only six molecules, and simple TFAs can be used to maintain a variety of MPs in native-like states in aqueous solutions.

Analyses of the new amphiphiles indicate they are superior to the commonly used biochemical detergent DDM with respect to several different protein systems. These results indicate that the new amphiphiles are at least complementary to current technology, such as known commercial biochemical detergents, in the context of the many membrane proteins that researchers would like to study. In general, a significant fraction of these proteins of interest remain very difficult to examine, and so new amphiphiles with distinctive structures and properties, such as those described herein, will be attractive as research tools.

A large number of amphiphiles are needed on the market for characterization and solubilization work, because many alternatives must be tried for each membrane protein to identify the best match. Accordingly, the amphiphiles described herein will provide additional resources to researchers for manipulating membrane proteins. For example, the amphiphiles can be used as reagents for protein solubilization and crystallization, especially for generally insoluble proteins. For a continuously updated database of MP structures, each of which can be potentially suitably manipulated by the TFAs described herein, see: http://blanco.biomol.uci.edu/Membrane_Proteins_xtal.html.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the invention, which is limited only by the appended claims.

DEFINITIONS

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element, including any variable, species of a variable, or a combination thereof. As such, this statement is intended to serve as antecedent basis for the use of exclusive terminology, such as "solely," "only," "not", and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percents, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible subranges and combinations of subranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into subranges as discussed above. In the same manner, all ratios recited herein also include all subratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

The phrase "treating a protein" with a compound, detergent, or surfactant ("agent") refers to contacting the protein with the agent (e.g., an amphiphile as described herein), and/or combining the protein with an effective amount of the agent under conditions that allow the agent to penetrate, integrate and/or disrupt a protein's current environment in order to solubilize, stabilize, isolate, and/or purify the protein. The conditions can be aqueous and additional reagents, such as buffers, salts, and the like, can be added. Thus, a combination of reagents may be employed in the treatment. The protein may be, for example, in a lipid bilayer or substantially isolated in solution.

An "effective amount" refers to an amount effective to bring about a recited effect. For example, an amount effective can be an amount of a reagent effective to solubilize or stabilize a membrane protein.

The term "alkyl" refers to a branched or unbranched hydrocarbon having, for example, from 1-20 carbon atoms, and often 1-12, 1-10, 1-8, 1-6, or 1-4 carbon atoms. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be a monovalent hydrocarbon radical, as described and exemplified above, or it can be a divalent hydrocarbon radical (i.e., an alkylene), according to the context of its usage.

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl group can be monovalent or divalent, and can be optionally substituted, for example, by one or more alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "saccharide" refers to a sugar or sugar moiety, such as a monosaccharide, a disaccharide, or a trisaccharide. Typical monosaccharides include allose, altrose, glucose, mannose, gulose, idose, galactose, or talose. Typical disaccharides include galactose, lactose, maltose, sucrose, trehalose, and cellobiose. Disaccharides can have any suitable linkage between the first and the second unit of the disaccharide. Other suitable saccharides include glucuronic acid, sorbase, ribose, and the like. A saccharide can include hydroxyl protecting groups such as, but not limited to, acetyl groups, benzyl groups, benzylidene groups, silyl groups, methoxy ether groups, or combinations thereof. The saccharide groups can also be in pyranose form, furanose form, or linear form. The saccharides can be linked to Formula I via their anomeric oxygen, or to any other available hydroxyl group. Depending on the context, as would be understood by one of skill in the art, the saccharide can include the oxygen that links it to another group, or exclude the oxygen that links it to another group.

Trisaccharides are oligosaccharides composed of three monosaccharides with two glycosidic bonds connecting them. Similar to disaccharides, each glycosidic bond can be formed between any hydroxyl group on the component monosaccharides. The three monosaccharide components can have different bond combinations (regiochemistry) and stereochemistry (alpha- or beta-linkages) to provide trisaccharides that are various diastereomers. Examples of trisaccharides include nigerotriose, maltotriose, maltotriulose, and raffinose.

The "Critical Micelle Concentration" (CMC) refers to the concentration of a detergent (e.g., an amphiphile as described herein) in an aqueous solution at which the detergent molecules self-assemble into micelles. Below the CMC, detergents are mostly monomeric; above the CMC, micelle concentration increases linearly with detergent concentration. The CMC is dependent upon many factors and is detergent-specific. The CMC of a detergent can be determined experimentally by measuring the solubilization of a water-insoluble dye or fluorophore while varying the concentration of detergent. A CMC may also be determined by measuring the diminution of the surface tension of an aqueous solution as a function of detergent concentration (CMCs determined by either method correlate with each other). The CMC is determined by extrapolating the plot of solubilization vs. concentration (or surface tension vs. concentration) in the two linear regions above and below the CMC. Where the two lines intersect is the CMC. The CMC can also be determined by the method of Nugebauer, J. M. (1990), *Methods in Enzymology*, 182:239-253.

Tandem Facial Amphiphiles

A tandem facial amphiphile can be a compound of a formula described herein, such as any one of Formulas I-XIV. The following values and variables can apply to any one or more of Formulas I-XIV, as applicable in the context of each formula.

In some embodiments, L can be —$(CH_2)_n$—. The variable n can be, for example, 1, 2, 3, 4, 5, 6, 7, 8, 9, or 10. In another embodiment, L can be a cycloalkyl diradical, such as a disubstituted cyclopentane, disubstituted cyclohexane, disubstituted cycloheptane, or disubstituted cyclooctane. In other embodiments, L can be a phenyl diradical. The phenyl diradical can be a 1,2-, 1,3-, or 1,4-diradical. In some embodiments, the phenyl can be substituted, such as with 1, 2, 3, or 4 $(C_1-C_4)$alkyl groups, e.g., a p-xylyl group.

In some embodiments, n is not 1, n is not 1 or 2, n is not 1-3, or n is not 1-4. In certain embodiments, n is at least 3, 4, 5, or 6 when one or both X groups is $CH_2$. In some embodiments, n is not 3. In some embodiments, n is 1-10 and $R^1$ is $(C_5\text{-}C_{20})$ alkyl. In some embodiments, $R^4$ is H. In various embodiments, m=0. In certain embodiments, one X is not $CH_2$. In other embodiments, both X groups are not $CH_2$.

In some embodiments, L can be a $-C(R^X)_2-$; or $-CH_2-C(R^X)_2-CH_2-$ linking group. Each $R^x$ can independently be H, OH, or $-CH_2O$-Sac. When $R^x$ is $-CH_2O$-Sac, it can be represented by $-CH_2-R^2$ where $R^2$ is O-Sac.

In some embodiments, each m is 0. In other embodiments, m is 1. When m is 0, Y is typically $CH_2$, although it can also be a direct bond. When m is 1, Y is typically a direct bond, although it can also be $CH_2$.

In some embodiments, each $R^1$ is H. When $R^1$ is H, the compounds typically make good hydrogel compositions with water. In other embodiments, each $R^1$ is $(C_1\text{-}C_{20})$alkyl. When $R^1$ is $(C_1\text{-}C_{20})$alkyl, the alkyl can be straight chain, branched, or optionally substituted. Examples of $(C_1\text{-}C_{20})$alkyl groups include the groups recited in the definition of alkyl.

In some embodiments, each X is O. In other embodiments, each X is S. In other embodiments, each X is NH. In yet other embodiments, each X is $CH_2$. In further embodiments, X can be a triazole diradical or a direct bond.

Each $R^2$, $R^3$, and $R^4$ can independently be H, OH, or O-Sac, such that each amphiphile includes at least 4 Sac moieties. Each Sac is independently an oxygen-linked monosaccharide, disaccharide, or trisaccharide. Specific examples of Sac groups are recited in the definition of the term saccharide.

In one specific embodiment, the compound has 4 Sac groups.

In another specific embodiment, the compound has 6 Sac groups.

In another specific embodiment, the compound has 8 Sac groups.

In one specific embodiment, each m is 1 and Y is a direct bond.

In one specific embodiment, each $R^1$ is $(C_1\text{-}C_{20})$alkyl.

In one specific embodiment, each X is a direct bond.

In one specific embodiment, L is $-(CH_2)_n-$ where n is 1-6.

In one specific embodiment, Y is a direct bond.

In one specific embodiment, $R^4$ is H.

In one specific embodiment, $R^2$ and $R^3$ are O-Sac and each Sac is a disaccharide.

In one specific embodiment, $R^2$ and $R^3$ are O-Sac and each Sac is a maltosyl group.

The compound of Formula I can be a compound of any one of Formulas II-XIV.

In another specific embodiment, the compound is a compound of Formula IV where each $R^1$ is $(C_1\text{-}C_8)$alkyl. In other specific embodiments, each $R^1$ is $CH_3$; $CH_2CH_3$; $CH_2(CH_3)_2$; $(CH_2)_3CH_3$; or $(CH_2)_4CH_3$.

In one specific embodiment, the compound is a compound of Formula VII (i.e., Formula I where m is 0 and Y is $CH_2$), where each X is independently O, S, NH, $CH_2$, or triazole; and n is −1, 0, 1, 2, 3, 4, 5, or 6.

In one specific embodiment, the compound is a compound of Formula VIII where each X is S, O, $CH_2$, or a triazole diradical, such as

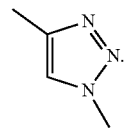

In another specific embodiment, the compound is a compound of Formula IX where each $R^2$ is independently a monosaccharide, disaccharide, trisaccharide, In one specific embodiment, each Sac is a monosaccharide. In another specific embodiment, each Sac is a monosaccharide or a disaccharide. In another specific embodiment, each Sac is a trisaccharide.

In another specific embodiment, the compound is a compound of Formula XII where each $R^2$ is independently an oxygen linked monosaccharide, disaccharide, trisaccharide, for example glucose, maltose, or raffinose.

In some embodiments, $R^2$, $R^3$, and/or $R^4$ can be —O-glucosyl, —O-maltosyl, —O-galactosyl, and the like. In certain embodiments, one or more of $R^2$, $R^3$, and/or $R^4$ can exclude —O-maltosyl groups.

In another specific embodiment, the compound is:

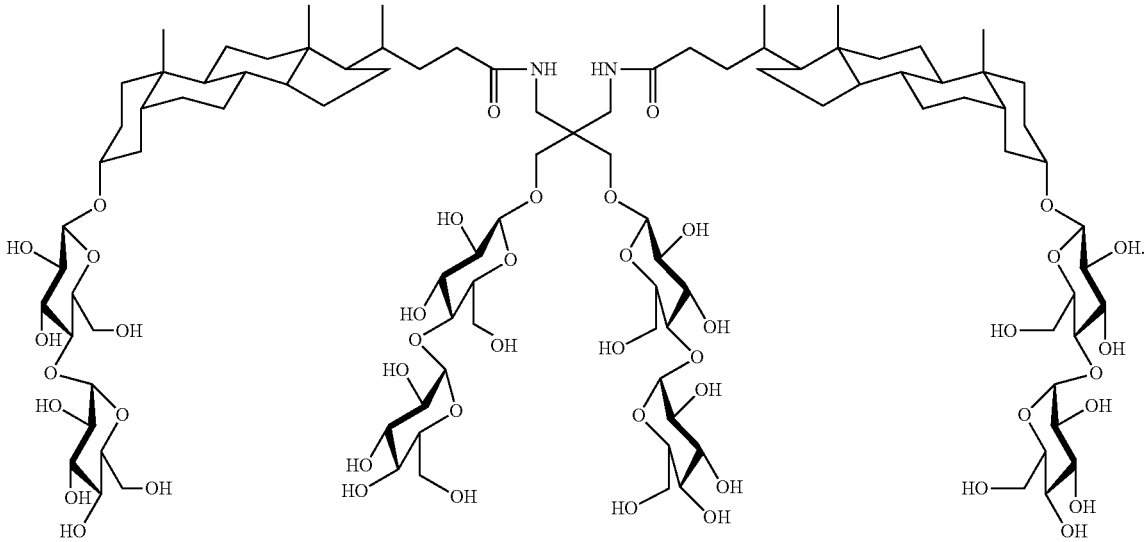

(IV-1)

In another specific embodiment, the compound is:

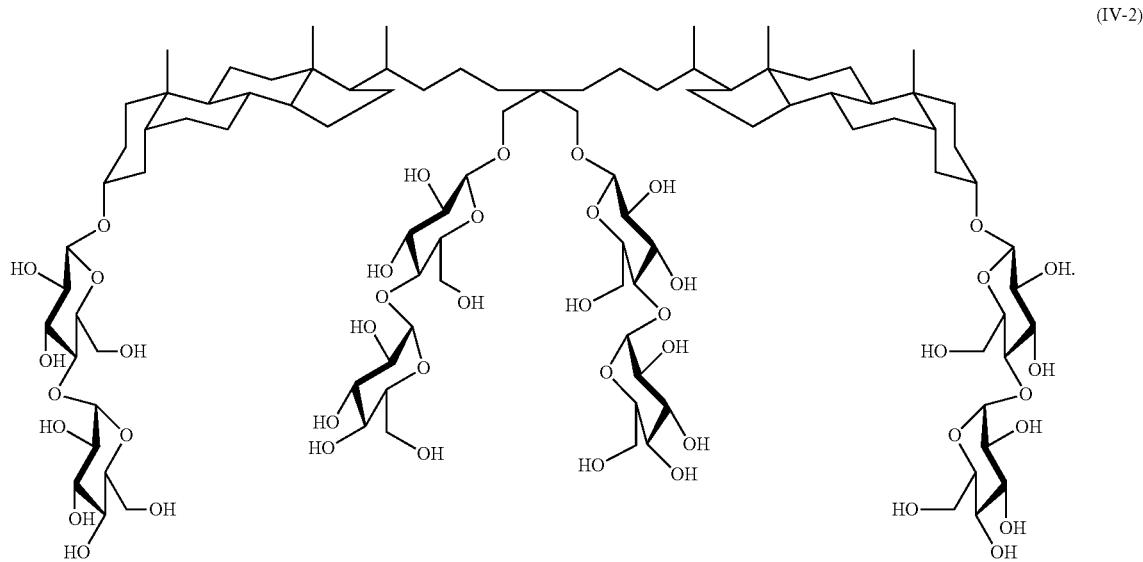

(IV-2)

In one specific embodiment, the compound is a compound of Formula XIV where each $R^2$ is independently a monosaccharide, disaccharide, trisaccharide, for example glucose, maltose, or raffinose.

In another specific embodiment, the compound is:

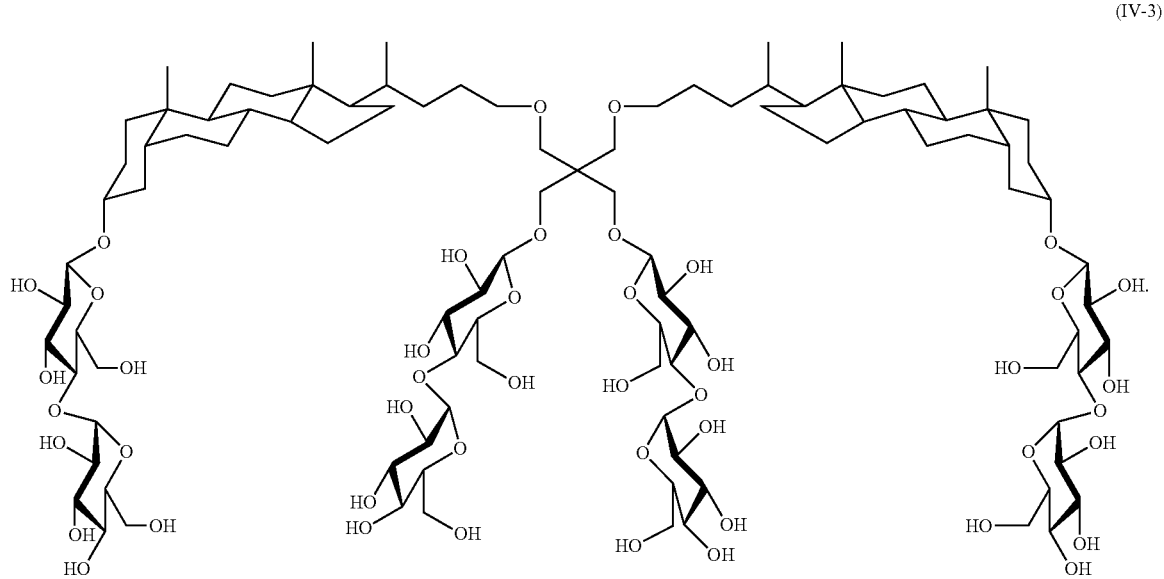

(IV-3)

can include about 6 to about 20 molecules of the compound, or about 6 to about 15 molecules, or about 6 to about 9 molecules.

In a further embodiment, the invention provides a composition that includes a plurality of compounds described herein and an isolated membrane protein in an aqueous medium. The composition can optionally include a buffer and one or more other surfactants.

Preparation of TFAs

Figure 2:
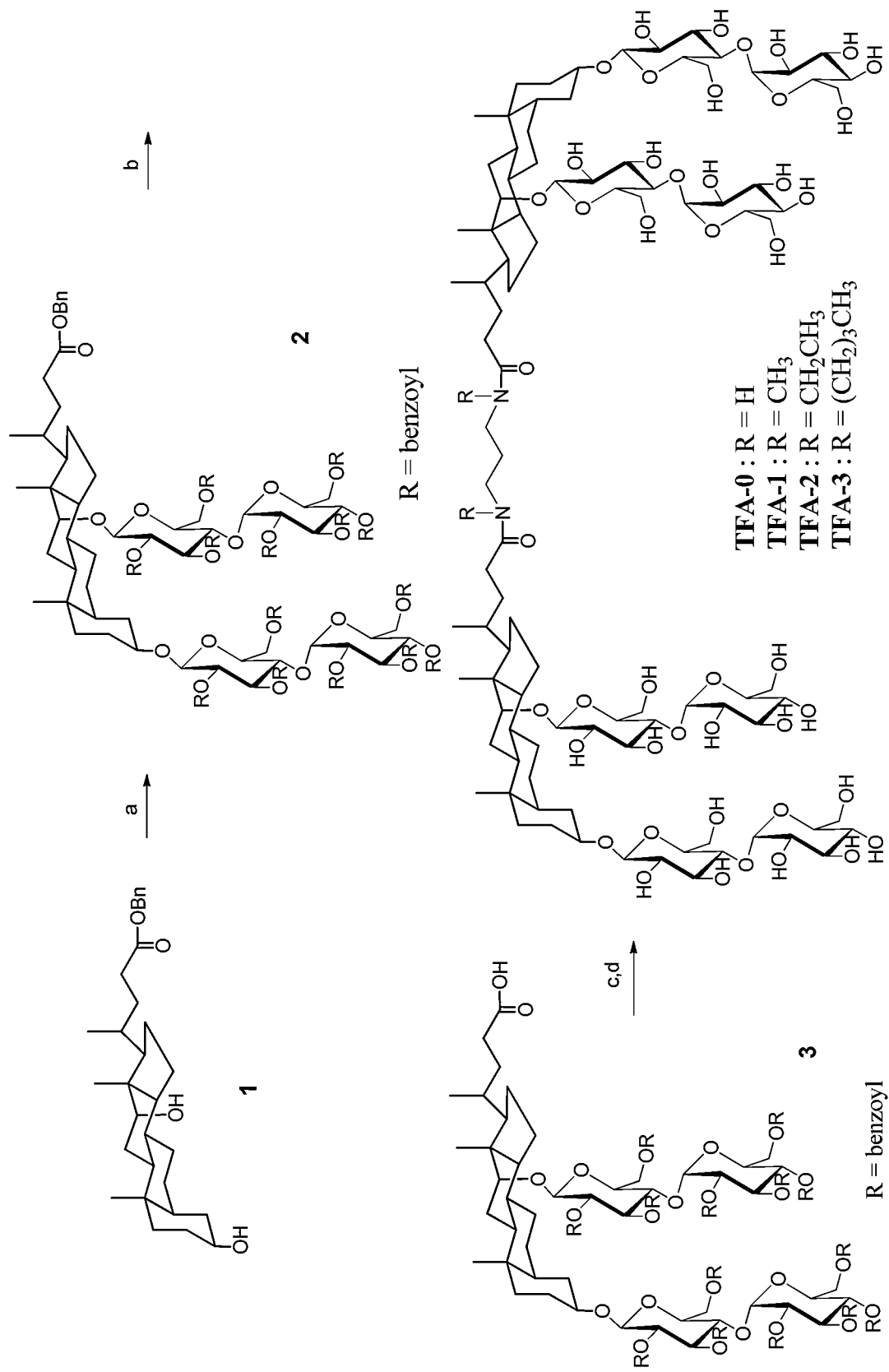
FIG. 2. Methods for the preparation of tandem facial amphiphiles; (a) perbenzoylated maltosylbromide, AgOTf, $CH_2Cl_2$, −45° C.→room temperature (~23° C.), 3 hr; (b) $NH_4^+CO_2^-$, Pd/C, EtOAc/MeOH, room temperature, 1 hr; (c) EDC.HCl, HOBt, room temperature, 2 days; (d) NaOMe, MeOH, room temperature, 4 hr.

The tandem facial amphiphiles (TFAs) can be prepared as illustrated in FIG. 2. For example, a protected cholate or deoxycholate can be conjugated to one or more optionally protected saccharide moieties by a suitable glycosylation reaction:

In certain embodiments, the critical micelle concentration (CMC) of the compound in water can be about 4 µM to about 20 µM, for example, about 4 µM to about 15 µM, or 5 µM to about 12 µM, such as about 6 µM or about 8 µM. The hydrodynamic radii ($R_h$) of micelles of the compound in water can be about 1.8 nm to about 3.4 nm. In some embodiments, the hydrodynamic radii ($R_h$) of micelles of the compound in water can be less than about 3.3 nm. In various embodiments, a plurality of the compounds form a micelle in water. The micelle can include as few as six molecules. Other micelles

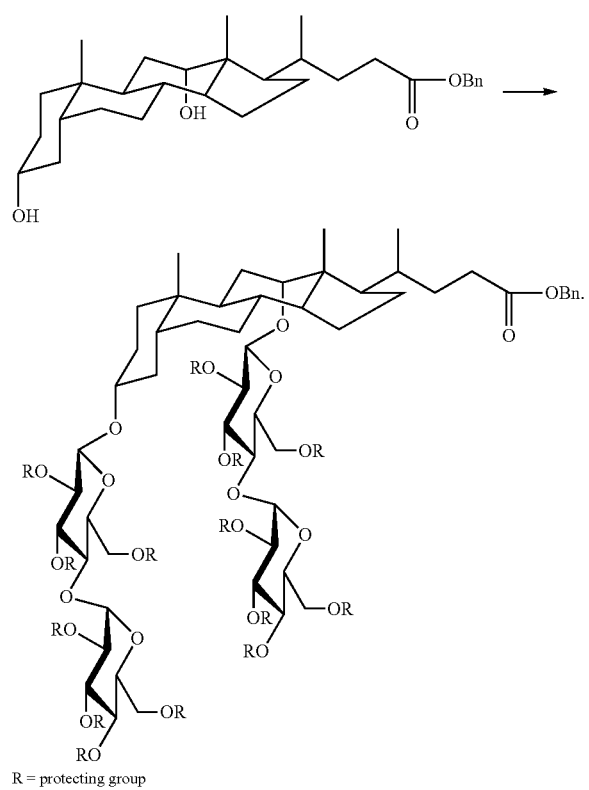

R = protecting group

The saccharide moieties can be maltose, as illustrated above, or they can be other saccharides, such as one or more of the monosaccharides, disaccharides, or trisaccharides recited herein. The saccharides can include various protecting groups, as would be well understood by one of skill in the art. Specific protecting groups include benzyl, acetyl, trifluoroacetyl, benzoyl, benzyloxycarbonyl, and silicon protecting groups such as trimethylsilyl, t-butyldimethylsilyl, and diphenylmethylsilyl. Other suitable protecting groups are known to those skilled in the art (see for example, T. W. Greene, *Protecting Groups In Organic Synthesis*; Wiley: New York, Third Edition, 1999, and references cited therein.

The protected carboxylic acid of the resulting conjugate can be deprotected, followed by formation of a dimer by coupling the glycosylated cholate or deoxycholate to a suitable linking group, such as 1,3-diaminopropane (or N-substituted analogs thereof) to form a bis-amide, using standard amide forming conditions. Finally, deprotection by removal of several or all of the hydroxyl protecting groups provides a TFA, suitable for membrane protein manipulation.

Standard synthetic transformations are well known in the art, and are generally described by reference works such as J. March, *Advanced Organic Chemistry, Reactions, Mechanisms and Structure*, (2nd Ed.), McGraw Hill: New York, 1977; Greg T. Hermanson in *Bioconjugate Techniques* (Academic Press, San Diego, Calif. (1996)); and F. Carey and R. Sundberg, *Advanced Organic Chemistry, Part B: Reactions and Synthesis*, (2nd Ed.), Plenum: New York, 1977; and references cited therein). Other useful synthetic techniques are described in U.S. Pat. No. 6,172,262 (McQuade et al.) and U.S. Patent Publication Nos. 2009/0270598 (Gellman et al.) and 2010/0311956 (Gellman et al.).

Another example of a tandem facial amphiphile is compound II-1:

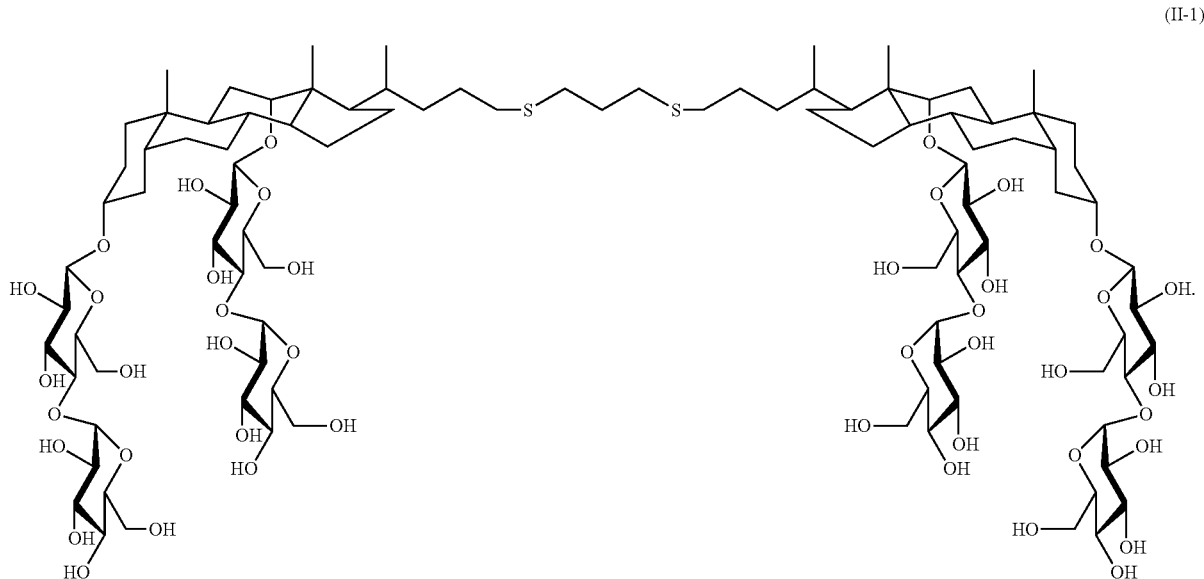

(II-1)

Compound II-1 can be prepared as illustrated in Scheme 1 below.

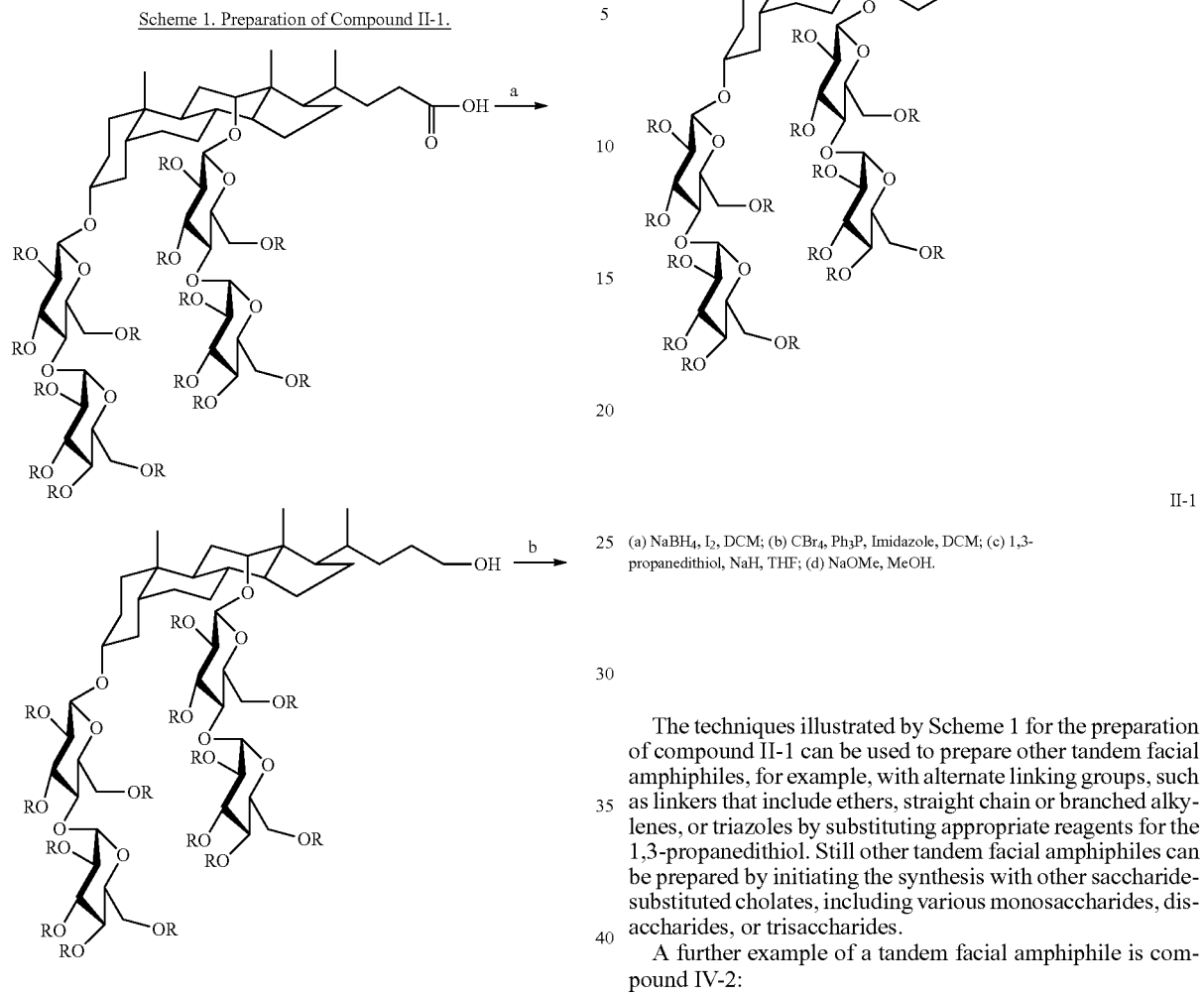

(a) NaBH$_4$, I$_2$, DCM; (b) CBr$_4$, Ph$_3$P, Imidazole, DCM; (c) 1,3-propanedithiol, NaH, THF; (d) NaOMe, MeOH.

The techniques illustrated by Scheme 1 for the preparation of compound II-1 can be used to prepare other tandem facial amphiphiles, for example, with alternate linking groups, such as linkers that include ethers, straight chain or branched alkylenes, or triazoles by substituting appropriate reagents for the 1,3-propanedithiol. Still other tandem facial amphiphiles can be prepared by initiating the synthesis with other saccharide-substituted cholates, including various monosaccharides, disaccharides, or trisaccharides.

A further example of a tandem facial amphiphile is compound IV-2:

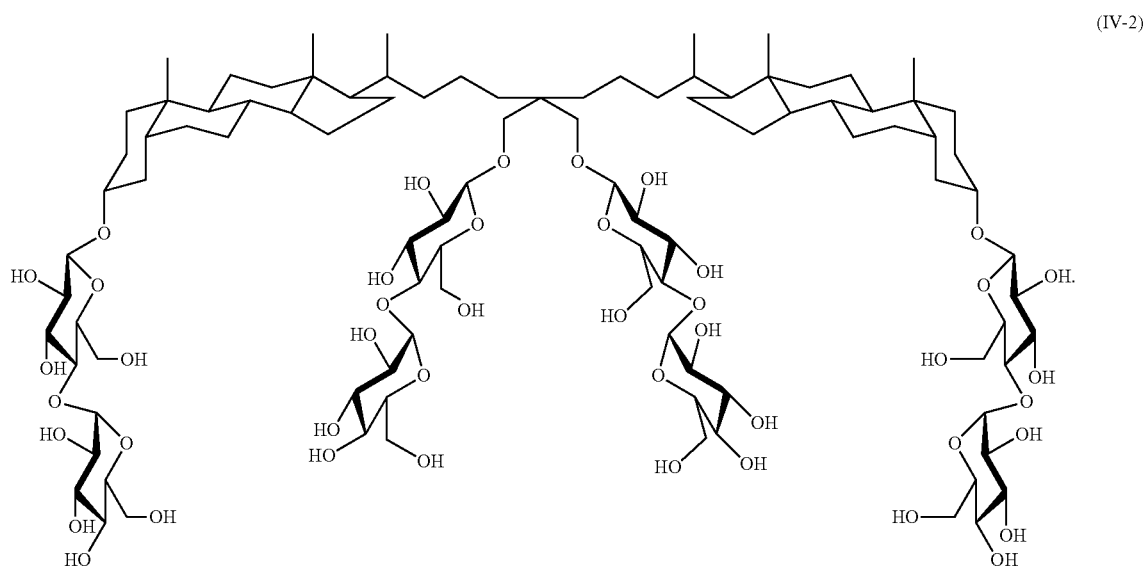

Compound IV-1 can be prepared as illustrated in Scheme 2 below.

Such compositions can take the form of aggregates or micelles, formed from a plurality amphiphilic compounds as

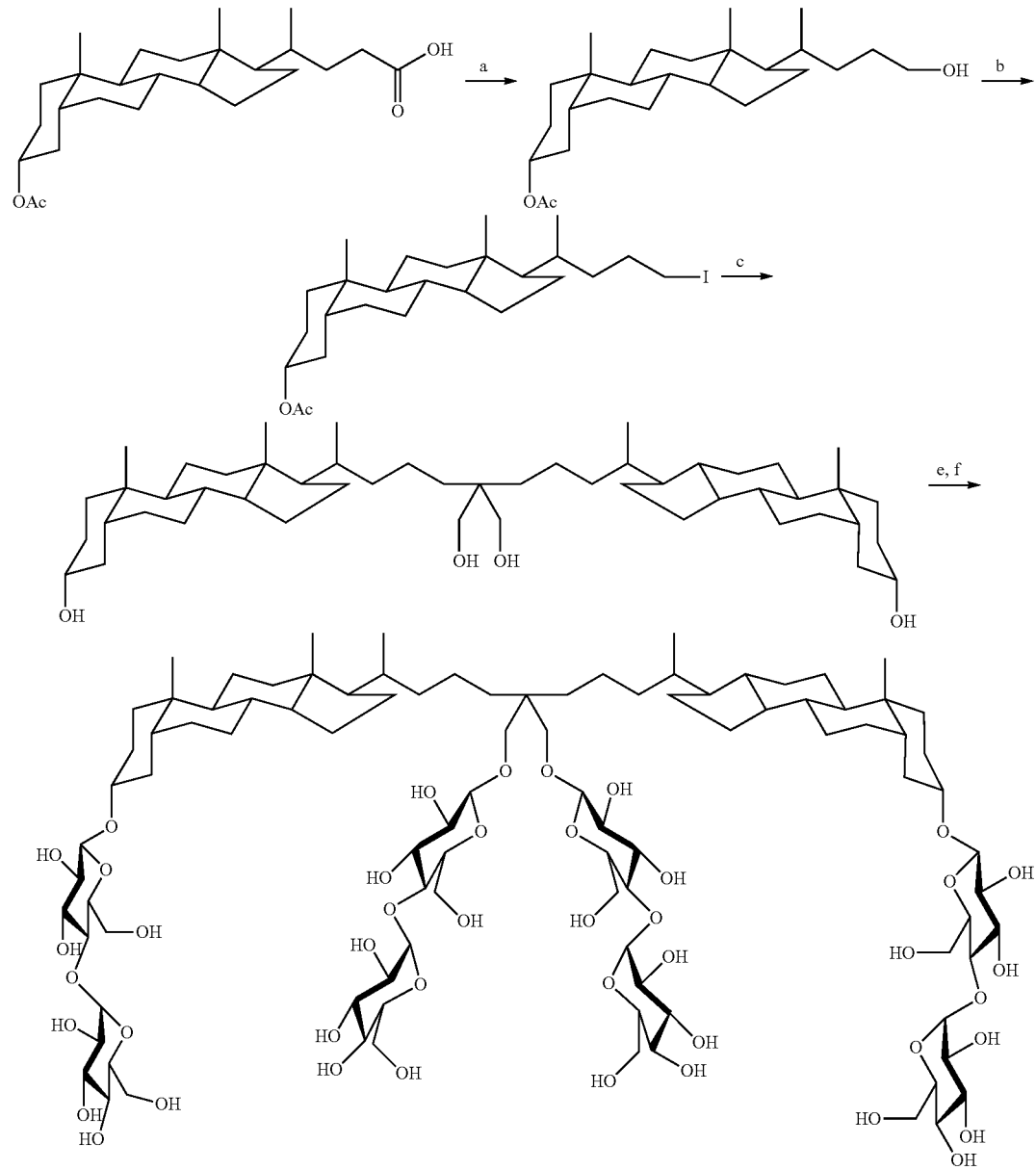

Scheme 2. Preparation of Compound IV-2.

(a) NaBH$_4$, I$_2$, DCM; (b) I$_2$, Ph$_3$P, Imidazole, MeCN; (c) diethylmalonate, NaH, THF; (d) LiAlH$_4$, THF; (e) perbenzoylated maltosyl bromide, AgOTf, DCM; (f) NaOMe, MeOH The techniques illustrated by Scheme 2 for the preparation of compound IV-2 can be used to prepare other tandem facial amphiphile with alternate linking groups, such as linkers that include various monosaccharides, disaccharides, or trisaccharides by conjugating the tetraol intermediate with the corresponding perbenzoylated (or otherwise protected) monosaccharides, disaccharides, or trisaccharides. Other synthetic procedures are outlined in the Examples below.

Applications of TFAs

The invention provides compositions that can include a plurality of amphiphilic compounds described herein and a membrane protein, such as an integral membrane protein.

described herein, optionally in conjunction with one or more other micelle-forming compounds, where the plurality of compounds surround the membrane protein. The composition can optionally include a polypeptide, a protein, and/or one or more other types of biological molecules complexed with the TFA compound.

The invention thus provides methods of solubilizing a membrane protein by contacting the membrane protein with a plurality of a compound described herein, in an aqueous solution, thereby forming a solubilized aggregation of the compounds and the membrane protein. The invention also provides methods of stabilizing a membrane protein by contacting the membrane protein with a plurality of a compound described herein, in an aqueous solution, thereby forming an aggregation of the compounds and the membrane protein. The invention further provides methods of extracting a protein from a lipid bilayer by contacting the lipid bilayer with a plurality of a compound described herein in an aqueous solution to form a mixture, optionally in the presence of a buffer or other detergent, thereby forming an aggregation of the compounds and the membrane protein extracted from the lipid bilayer. The aggregation can then be separated from the mixture to provide isolated and/or purified membrane protein.

The invention thus provides methods for manipulating membrane proteins. For example, a method is provided for solubilizing a membrane protein by contacting the protein in an aqueous environment with an effective amount of a compound as described herein, and optionally heating the protein and the compound, to provide the solubilized protein encapsulated in micelles of the compound. The effective amount of the compound can be an amount of the compound necessary to achieve its critical micelle concentration, to about 10 times, about 100 times, about 1,000 times, or about 10,000 times, the amount of the compound necessary to achieve its critical micelle concentration. The method can also include employing a buffer, a second amphiphile or detergent, or other reagents, in the aqueous environment to aid in the solubilization and stabilization of membrane proteins.

The invention also provides a method of purifying a membrane protein by contacting the protein in an aqueous environment with an effective amount of a compound as described herein, to form micelles comprising a plurality of the compounds surrounding the protein, and isolating the micelles, to provide the purified membrane protein encapsulated in micelles of the compound. Other techniques for using the amphiphilic compounds described herein include techniques for stabilizing, crystallizing, and/or characterizing a protein while in a detergent micelle made up of a compound described herein.

The invention has several advantages over previous membrane manipulation technologies. For example, the amphiphiles described herein can lack any aromatic groups, therefore they are highly suitable for "optical" characterization methods such as UV absorbance spectroscopy and UV circular dichroism, when characterizing a protein solubilized by such amphiphiles.

Other uses of the amphiphiles described herein include their use as amphiphilic additions in crystallization trials, components of detergent mixtures, stabilizing factors in functional assays, detergents in exchange schemes, solubilization agents in cell-free expression reactions, as well as their use for separation on polyacrylamide gels using native protocols to maintain native states, for use in sample buffers on membrane fractions used to solubilize membrane proteins and to prepare proteins for separation on gels, and for use with Bug Buster® Protein Extraction Reagent formulations designed to break open cells and survey protein present, for example, without using sonication and/or lysozyme treatment and osmotic shock, such as with eukaryotic cell pellets that are relatively fragile and easily disrupted.

The amphiphiles described herein can also aid the formation of well-ordered crystals of membrane protein-amphiphile complexes. When a membrane protein-amphiphile complex crystallizes, amphiphiles can be included within the crystal lattice or in other embodiments, excluded from the crystal lattice. The amphiphiles can contribute to the ordering of proteins within the lattice when crystals are formed, thereby aiding the stability of growing membrane protein crystals.

The TFAs can stabilize membrane proteins, such as integral membrane proteins, in native conformations, for example, for protein structural characterization. The TFAs can extract proteins from lipid bilayers and stabilize the protein comparably or more effectively than conventional biological detergents. The TFAs can further be used for membrane protein research including isolation, stabilization, analysis by solution NMR, and biochemical and biophysical assay development.

The invention can therefore be directed to amphiphiles that can enhance the ability of a composition to solubilize and crystallize membrane-bound proteins into well-order crystals. The TFAs described herein can also be used in any application where conventional detergents are used. For instance, the TFAs can be used to lyse cellular membranes. The TFAs can also form micelles in an aqueous solution. They can therefore be used to solubilize hydrophobic compounds for dispersion into aqueous solution. More specifically, the TFAs are useful for solubilizing membrane proteins, such as integral membrane proteins.

The TFAs described herein can be used alone, or in combination with other biological detergents, such as DDM, undecyl-β-D-maltoside (β-UDM), 3-[(3-cholamidopropyl)-dimethylammonio]-1-propanesulfonate (CHAPS), 3-[(3-cholamidopropyl)-dimethylammonio]-2-hydroxy-1-propanesulfonate (CHAPSO), lauryldimethylamine oxide, octyl-glucoside (OG) or other detergents described by Hjelmeland in *Methods of Enzymology*, Vol. 124, page 135-164, which is incorporated herein by reference. For example, a particular detergent may to too harsh to suitable solubilize a membrane protein in its native conformation, however a combination of a TFA described herein and a commercial biological detergents can provide reduced severity, thereby allowing the protein to be maintained in its native conformation while maintaining solubility.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Amphiphile Synthesis

Novel tandem facial amphiphiles were prepared as illustrated in FIG. 2. While reagents and reaction conditions can be varied, the methods of FIG. 2 were carried out using the following, as further described below: (a) perbenzoylated maltosylbromide, AgOTf, $CH_2Cl_2$, −45° C.→room temperature, 3 hr; (b) $NH_4^+CO_2^-$, Pd/C, EtOAc/MeOH, room temperature, 1 hr; (c) EDC.HCl, HOBt, room temperature, 2 days; (d) NaOMe, MeOH, room temperature, 4 hr.

Compound 2. This reaction was performed according to a literature method (Ashton et al., *Chem. Eur. J.* 2, 1115-1128 (1996)) with slight modification. A mixture of 1 (Vijayalakshmi et al., *Macromolecules* 39, 7931-7940 (2006)) (0.83 g, 1.7 mmol.), AgOTf (0.97 g, 3.8 mmol), 2,4,6-collidine (0.39 g, 2.9 mmol) in anhydrous $CH_2Cl_2$ (40 mL) was stirred at −45° C. A solution of perbenzoylated maltosylbromide (4.3 g, 3.8 mmol) in CH$_2$Cl$_2$ (40 mL) was added dropwise over 0.5 h to this suspension. Stirring was continued for 0.5 h at −45° C., and then the reaction mixture was rapidly warm to 25° C. and left stirring for 3 h. After completion of reaction (as detected by TLC analysis), pyridine was added to the reaction mixture, and it was diluted with CH$_2$Cl$_2$ (40 mL) before being filtered over celite. The filtrate was washed successively with a 1 M aqueous Na$_2$S$_2$O$_3$ solution (40 mL), a 0.1 M aqueous HCl solution (40 mL), and brine (2×40 mL). Then the organic layer was dried with anhydrous Na$_2$SO$_4$ and the solvents were removed by rotary evaporation. The residue was purified by silica gel column chromatography (EtOAc/hexane) providing desired product (2) as a glassy solid (3.2 g, 72%). $^1$H NMR (300 MHz, CDCl$_3$): δ 8.13-8.05 (m, 4H), 8.05-7.92 (m, 12H), 7.90-7.84 (m, 8H), 7.62-7.82 (m, 22H), 7.62-7.05 (m, 99H), 6.10 (q, J=10.1 Hz, 4H), 5.84-5.60 (m, 12H), 5.40-5.22 (m, 8H), 5.08-4.82 (m, 8H), 4.75-4.18 (m, 20H), 4.18-4.04 (m, 4H), 4.04-3.92 (m, 2H), 3.76 (br s, 2H), 3.55-3.40 (m, 2H), 2.05-1.95 (m, 2H), 1.95-1.80 (m, 6H), 1.80-1.00 (m, 52H), 1.00-0.72 (m, 28H), 0.70-0.60 (m, 10H), 0.60-0.45 (m, 6H); $^{13}$C NMR (75 MHz, CDCl$_3$): δ 173.6, 166.4, 166.1, 165.8, 165.7, 165.6, 165.4, 165.2, 165.1, 164.9, 133.6, 133.5, 133.4, 133.3, 133.2, 133.1, 130.2, 130.1, 130.0, 129.9, 129.8, 129.6, 129.2, 129.1, 129.0, 128.9, 128.7, 128.6, 128.5, 128.4, 128.3, 128.2, 102.7, 100.1, 96.9, 96.8, 85.4, 81.5, 77.4, 75.2, 75.3, 74.8, 74.1, 73.2, 72.8, 71.4, 70.9, 70.3, 70.2, 69.5, 69.4, 69.3, 69.2, 66.0, 62.9, 53.6, 48.0, 47.1, 46.8, 42.5, 36.4, 35.5, 35.3, 34.6, 34.5, 34.0, 32.2, 29.5, 27.7, 26.1, 24.0, 23.4, 17.2, 12.6; MS (MALDI-TOF): calcd. for C$_{153}$H$_{142}$O$_{38}$ [M+Na]$^+$ 2611.7. found 2611.4.

Compound 3. This reaction was performed according to a literature method (Roy et al., *Can. J. Chem.* 69, 817-821 (1991)) with slight modification. Compound 2 (0.85 g, 0.33 mmol), 10% Pd/C (0.17 g) and ammonium formate (0.21 g, 3.28 mmol) were suspended in MeOH:EtOAc (15 mL:9 mL). The solution was stirred for 1 h at 25° C. The solution was filtered through celite, which was rinsed with MeOH, and the solution was evaporated to give desired product (3) as a glassy solid (0.80 g, 98%). $^1$H NMR (300 MHz, CDCl$_3$): δ 8.13-8.05 (m, 4H), 8.05-7.92 (m, 12H), 7.90-7.84 (m, 8H), 7.62-7.82 (m, 22H), 7.62-7.05 (m, 94H), 6.10 (q, J=10.1 Hz, 4H), 5.84-5.60 (m, 12H), 5.40-5.22 (m, 8H), 5.08-4.82 (m, 8H), 4.75-4.18 (m, 20H), 4.18-4.04 (m, 4H), 4.04-3.92 (m, 2H), 3.76 (br s, 2H), 3.55-3.40 (m, 2H), 2.05-1.95 (m, 2H), 1.95-1.80 (m, 6H), 1.80-1.00 (m, 52H), 1.00-0.72 (m, 28H), 0.70-0.60 (m, 10H), 0.60-0.45 (m, 6H); $^{13}$C NMR (75 MHz, CDCl$_3$): δ 178.9, 166.4, 166.1, 166.0, 165.9, 165.8, 165.4, 165.3, 165.2, 164.9, 133.5, 133.4, 133.3, 133.2, 133.0, 130.2, 130.1, 130.0, 129.9, 129.8, 129.7, 129.6, 129.5, 129.4, 129.3, 129.2, 129.1, 129.0, 128.7, 128.6, 128.5, 128.4, 128.3, 128.2, 128.0, 127.9, 110.9, 102.7, 100.1, 96.9, 96.8, 85.3, 81.5, 77.4, 75.6, 75.3, 74.8, 74.2, 73.2, 73.1, 72.8, 71.5, 71.0, 70.3, 70.2, 69.5, 69.4, 69.3, 69.2, 64.2, 62.9, 48.0, 47.1, 46.9, 42.5, 36.4, 35.6, 34.6, 34.5, 34.0, 31.8, 29.4, 27.8, 27.7, 27.6, 23.5, 17.3, 12.7; MS (MALDI-TOF): calcd. for C$_{146}$H$_{136}$O$_{38}$ [M+Na]$^+$ 2521.6. found 2521.1.

TFA-0. Compound 3 (900 mg, 0.36 mmol), 1,3-diaminopropane (15 mg, 0.17 mmol), 1-hydroxybenzotriazole monohydrate (HOBt) (58 mg, 0.43 mmol) was dissolved in anhydrous DMF (30 mL). 1-(3-(dimethylamino)propyl)-3-ethylcarbodiimide hydrochloride (EDC.HCl) (83 mg, 0.43 mmol) was added in small portions at 0° C. and the resulting solution left stirring at room temperature for 48 h. The solution was taken up with EtOAc (100 mL) and was washed successively with a 1 M aqueous NaHCO$_3$ solution (100 mL), a 0.1 M aqueous HCl solution (100 mL) and brine (2×100 mL). Then the organic layer was dried with anhydrous Na$_2$SO$_4$ and the solvent was removed by rotary evaporation, and used in next reaction without further purification. The resulting O-benzoylated compounds were dissolved in MeOH and then treated with the required amount of a methanolic solution of 0.5 M NaOMe such that the final concentration of NaOMe was 0.05 M. The reaction mixture was left stifling for 6 h at room temperature, and then neutralized with Amberlite IR-120 (H$^+$ form) resin. The resin was removed by filtration and washed with MeOH and solvent was removed from the combined filtrate in vacuo. The residue was purified by silica gel column chromatography (MeOH/CH$_2$Cl$_2$). Further purification carried out by recrystallization using CH$_2$Cl$_2$/MeOH/diethyl ether afforded fully de-O-benzoylated product (TFA-0) as a white solid (0.69 g, 90%). $^1$H NMR (300 MHz, CD$_3$OD): δ 5.22 (d, J=3.8 Hz, 2H), 5.19 (d, J=3.8 Hz, 2H), 4.45 (d, J=7.6 Hz, 2H), 4.39 (d, J=7.6 Hz, 2H), 3.96-3.78 (m, 14H), 3.78-3.58 (m, 20H), 3.58-3.45 (m, 10H), 3.45-3.15 (m, 12H), 2.36-2.06 (m, 8H), 2.04-1.82 (m, 10H), 1.82-1.53 (m, 14H), 1.53-1.35 (m, 12H), 1.35-1.05 (m, 14H), 1.05-0.88 (m, 8H), 0.74 (s, 6H) 7; $^{13}$C NMR (75 MHz, CD$_3$OD): δ 177.5, 106.7, 103.1, 102.8, 102.4, 86.2, 81.8, 81.5, 80.6, 78.3, 78.0, 76.7, 75.5, 75.2, 74.9, 74.8, 74.3, 71.7, 71.6, 62.9, 62.4, 46.3, 43.9, 37.9, 37.6, 37.5, 36.6, 35.8, 35.6, 35.3, 33.8, 33.3, 30.4, 29.3, 28.6, 28.5, 28.4, 27.8, 25.2, 23.9, 18.2, 13.0; MS (MALDI-TOF): calcd. for C$_{99}$H$_{166}$N$_2$O$_{46}$ [M+Na]$^+$ 2142.0. found 2142.1.

TFA-1: N,N'-dimethyl-1,3-propanediamine was used instead of 1,3-diaminopropane in the synthesis of TFA-0. $^1$H NMR (300 MHz, CD$_3$OD): δ 5.22 (d, J=3.8 Hz, 2H), 5.19 (d, J=3.8 Hz, 2H), 4.45 (d, J=7.6 Hz, 2H), 4.40 (d, J=7.6 Hz, 2H), 3.96-3.78 (m, 14H), 3.78-3.58 (m, 20H), 3.58-3.20 (m, 22H), 3.10 (d, J=10.3 Hz, 4H), 2.95 (d, J=10.7 Hz, 2H), 2.36-2.06 (m, 8H), 2.04-1.82 (m, 10H), 1.82-1.53 (m, 14H), 1.53-1.35 (m, 12H), 1.35-1.05 (m, 14H), 1.05-0.88 (m, 8H), 0.76 (s, 6H); $^{13}$C NMR (75 MHz, CD$_3$OD): δ 176.9, 176.7, 176.6, 106.8, 103.0, 102.7, 102.4, 86.2, 81.6, 81.4, 80.6, 78.2, 77.9, 76.7, 75.4, 75.2, 74.9, 74.8, 74.3, 71.6, 63.2, 62.9, 62.4, 46.7, 46.3, 43.8, 37.6, 37.5, 37.4, 36.6, 36.4, 35.7, 35.6, 35.3, 33.9, 32.6, 31.2, 29.3, 28.7, 28.5, 27.8, 25.3, 23.9, 18.4, 18.3, 13.0; MS (MALDI-TOF): calcd. for C$_{101}$H$_{170}$N$_2$O$_{46}$ [M+Na]$^+$ 2170.1. found 2170.0.

TFA-2: N,N'-diethyl-1,3-propanediamine was used instead of 1,3-diaminopropane in the synthesis of TFA-0. $^1$H NMR (300 MHz, CD$_3$OD): δ 5.22 (d, J=3.8 Hz, 2H), 5.19 (d, J=3.8 Hz, 2H), 4.45 (d, J=7.6 Hz, 2H), 4.40 (d, J=7.6 Hz, 2H), 3.96-3.78 (m, 14H), 3.78-3.58 (m, 20H), 3.58-3.20 (m, 26H), 2.36-2.06 (m, 8H), 2.04-1.82 (m, 10H), 1.82-1.53 (m, 14H), 1.53-1.35 (m, 12H), 1.35-1.05 (m, 14H), 1.05-0.88 (m, 8H), 0.76 (s, 6H); $^{13}$C NMR (75 MHz, CD$_3$OD): δ 176.5, 176.4, 176.2, 106.7, 103.0, 102.8, 102.5, 98.6, 86.2, 81.6, 81.4, 80.6, 78.3, 78.0, 76.7, 75.5, 75.2, 74.9, 74.8, 74.3, 74.2, 71.7, 71.6, 63.2, 62.9, 62.4, 55.3, 48.3, 48.1, 46.5, 44.4, 43.9, 37.6, 36.6, 35.8, 35.6, 35.3, 29.4, 28.7, 28.5, 28.4, 27.8, 25.3, 23.9, 18.5, 18.4, 18.3, 14.8, 14.7, 13.4, 13.1, 13.0; MS (MALDI-TOF): calcd. for C$_{103}$H$_{174}$N$_2$O$_{46}$ [M+Na]$^+$ 2198.1. found 2198.0.

N,N'-dibutyl-1,3-propanediamine. Butyric acid (1.8 g, 19.4 mmol), 1,3-diaminopropane (0.60 g, 8.1 mmol), 1-hydroxybenzotriazole monohydrate (HOBt) (2.4 g, 17.8 mmol) was dissolved in anhydrous DMF (30 mL). 1-(3-(dimethylamino)propyl)-3-ethylcarbodiimide hydrochloride (EDC.HCl) (3.4 g, 17.8 mmol) was added in small portions at 0° C. and the resulting solution left stirring at room temperature for 15 h. After evaporation of DMF, the solution was taken up with CHCl$_3$ (200 mL) and was washed successively with a 1 M aqueous NaHCO$_3$ solution (30 mL), a 0.1 M aqueous HCl solution (30 mL) abd brine (30 mL). Then the organic layer was dried with anhydrous Na$_2$SO$_4$ and the solvent was removed by rotary evaporation. The resulting residue was precipitated using ether and used in next reaction without further purification. To the precipitate dissolved in THF (50 mL), LiAlH$_4$ (0.40 g, 10.6 mmol) was added slowly at 0° C. The mixture was refluxed overnight, quenched carefully with 0.4 mL of water, 0.4 mL of 15% NaOH and 1.2 mL of water. After filtration on celite, the filtrate was evaporated, dissolved in DCM (100 mL) and extracted with 1N NaOH solution (50 mL). The organic layer dried with anhydrous Na$_2$SO$_4$. The residue was purified by silica gel column chromatography (MeOH/CH$_2$Cl$_2$) providing N,N'-dibutyl-1,3-propanediamine as an oil (0.90 g, 52% (two steps)). $^1$H NMR (300 MHz, CDCl$_3$): δ 2.67 (t, J=7.0 Hz, 4H), 2.59 (t, J=7.0 Hz, 4H), 1.69 (quin, J=7.0 Hz, 2H), 1.52-1.39 (m, 4H), 1.39-1.24 (m, 4H), 0.91 (t, J=7.2 Hz, 6H); $^{13}$C NMR (75 MHz, CDCl$_3$): δ 50.1, 48.9, 32.5, 30.7, 20.7, 14.2; HRMS (ESI): calcd. for C$_{11}$H$_{26}$N$_2$[M+H]$^+$ 187.2169. found 187.2170.

TFA-3: N,N'-dibutyl-1,3-propanediamine was used instead of 1,3-diaminopropane in the synthesis of TFA-0. $^1$H NMR (300 MHz, CD$_3$OD): 5.22 (d, J=3.8 Hz, 2H), 5.19 (d, J=3.8 Hz, 2H), 4.50-4.37 (m, 4H), 4.00-3.78 (m, 14H), 3.78-3.56 (m, 20H), 3.56-3.18 (m, 26H), 2.54-2.10 (m, 8H), 2.04-1.85 (m, 10H), 1.85-1.55 (m, 16H), 1.55-1.23 (m, 22H), 1.23-1.06 (m, 10H), 1.06-0.86 (m, 14H), 0.77 (s, 6H); $^{13}$C NMR (75 MHz, CD$_3$OD): δ 176.7, 176.5, 176.4, 106.8, 106.7, 103.0, 102.8, 102.4, 86.1, 81.6, 81.4, 80.6, 78.3, 77.9, 76.7, 75.6, 75.4, 75.2, 74.9, 74.8, 74.3, 71.7, 71.6, 63.2, 62.9, 62.4, 62.4, 55.8, 46.9, 46.5, 44.9, 43.8, 37.6, 37.4, 36.6, 35.7, 35.6, 35.3, 33.3, 33.2, 32.6, 32.5, 31.1, 29.4, 28.7, 28.5, 28.4, 27.8, 25.3, 23.9, 21.4, 21.3, 21.2, 18.5, 18.4, 18.3, 14.5, 14.4, 13.1, 13.0; MS (MALDI-TOF): calcd. for C$_{107}$H$_{182}$N$_2$O$_{46}$[M+Na]$^+$ 2282.2. found 2282.2.

Example 2

Tandem Facial Amphiphiles

A set of four tandem facial amphiphiles (TFAs) was generated from a deoxycholate-bis-maltoside building block via linkage with a diaminopropane unit (FIGS. 1 and 2). Molecular mechanics calculations indicate that an extended conformation of the TFA backbone has a length that is comparable to the width of a typical lipid bilayer (~30 Å) (see Example 3 below). The TFAs can vary in the appendage on the amide nitrogen atoms. Each of the initial set of amphiphiles could be obtained in excellent purity (>98%) and good overall yield (~65%) in five straightforward synthetic steps with two chromatographic purifications. Multi-gram quantities are readily available.

The TFAs displayed interesting behavior in water. TFA-0 forms a hydrogel at concentrations >0.4 wt %, and this compound was not studied further. The other three TFAs are soluble to 5-10 wt % in aqueous media. Critical micelle concentrations (CMC) were determined by monitoring solubilization of a hydrophobic fluorescent dye, dicyclohexatriene (Chattopadhyay et al., *Anal. Biochem.* 1984, 139, 408-412), and the hydrodynamic radii (R$_h$) of the micelles were determined via dynamic light scattering (DLS). Table 1 compares the data for TFAs with those for DDM, a conventional detergent that is very widely used for MP applications; DDM and the TFAs share maltose as their hydrophilic moieties. CMC values of the three TFAs are smaller than that of DDM, whether CMC is measured in units of mM or wt %. The micelles formed by TFA-1 and TFA-2 (R$_h$~2.0 nm) are smaller than those formed by DDM, while micelles formed by TFA-3 are comparable to those of DDM (R$_h$~3.4 nm).

TABLE 1

CMC of TFAs and hydrodynamic radii (R$_h$) of their micelles (mean ± SD, n = 3).

|  | MW$^a$ | CMC (μM) | CMC (wt %) | R$_h$ (nm)$^b$ |
|---|---|---|---|---|
| TFA-1 | 2148.4 | 13 ± 1.4 | 0.0028 ± 0.00030 | 1.9 ± 0.08 |
| TFA-2 | 2176.5 | 13 ± 1.8 | 0.0028 ± 0.00039 | 2.0 ± 0.03 |
| TFA-3 | 2232.6 | 7 ± 2.3 | 0.0016 ± 0.00051 | 3.3 ± 0.12 |
| DDM | 510.1 | 170 | 0.0087 | 3.4 ± 0.03 |

$^a$ Molecular weight of detergents.
$^b$ Hydrodynamic radius of micelles measured by dynamic light scattering.

Micelles formed by DDM or by TFA-1 in pH 7.0 buffer (20 mM HEPES, 150 mM NaCl) were further characterized by gel filtration using a triple-detector system (Gatta et al., *Anal. Biochem.* 2010, 404, 21-29), analyzing light scattering, refractive index, and differential pressure (Table 2). In both cases the micelles are globular and monodisperse. TFA-1 micelles contain only 6 molecules, which contrasts with the ~175 molecules in a DDM micelle. TFA-2 (R=ethyl) behaved similarly to TFA-1 (R=methyl), given the similarity in R$_h$, but TFA-3 (R=butyl) forms larger micelles. A related trend was observed among lipopeptides, with increasing length of the alkyl appendages leading to increasing micelle size (McGregor et al., *Nat. Biotech.* 2003, 21, 171-176).

TABLE 2

Characterization of TFA-1 (mean ± SD, n = 6) and DDM micelles (mean ± SD, n = 8).

|  | MMW$^a$ | N$^b$ | R$_h$ (nm) | IV$^c$ | Mw/Mn$^d$ | dn/dc$^e$ |
|---|---|---|---|---|---|---|
| DDM | 89982 ± 663 | 176.4 ± 1.3 | 3.42 ± 0.04 | 0.028 ± 0.009 | 1.01 ± 0.00 | 0.130 |
| TFA-1 | 13279 ± 157 | 6.2 ± 0.07 | 1.96 ± 0.01 | 0.036 ± 0.005 | 1.00 ± 0.00 | 0.173 |

$^a$ Molecular weight of micelles.
$^b$ Aggregation number of micelles.
$^c$ Intrinsic viscosity.
$^d$ Weight-averaged molecular weight divided by number-averaged molecular weight.
$^e$ Specific refractive index increment.

Figure 3:
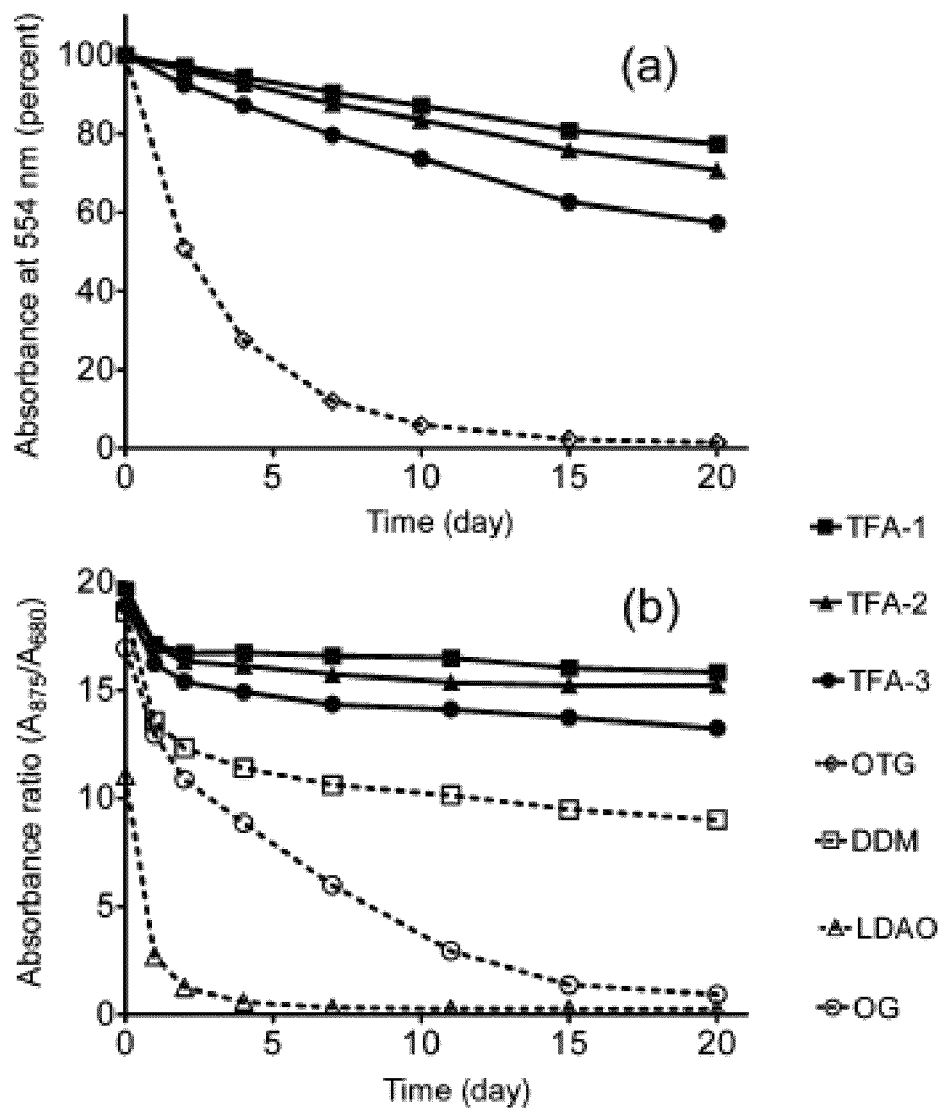
FIG. 3. Time course of the stability of bR (a) and R. capsulatus superassembly (b) at room temperature. Detergents were tested at 0.2 wt % OTG+0.8 wt % TFA and CMC+0.04 wt % for bR and R. capsulatus superassembly, respectively. OTG is octyl-β-D-thioglucoside.

Bacteriorhodopsin (bR) has been widely employed for assessment of new amphiphiles because this membrane protein is readily available, and stability can be assessed via spectrophotometry (absorbance at 554 nm). Following standard protocols (Bazzacco et al., *Biomacromolecules* 2009, 10, 3317-3326), 2.0 wt % octyl-β-D-thioglucoside (OTG) was used to extract bR from the native purple membrane. After removal of insoluble debris via ultracentrifugation, the bR solution was diluted with amphiphile-containing solutions to generate samples containing 0.2 wt % OTG+0.8 wt % TFA. A control sample had OTG added to give a total of 1.0 wt %. FIG. 3a shows that all three TFA-containing samples were much more effective at maintaining native bR absorbance over 20 days relative to the sample containing only OTG. The bR was almost completely denatured by day 10 in the OTG-only sample, but ~80% intact at day 20 when solubilized with TFA-1. Parallel studies were carried out at different amphiphile concentrations as described in Example 3 below. DDM is not efficient at bR extraction from the native membrane but extracted bR can be stable in the presence of DDM (Milder et al., *Biochemistry* 1991, 30, 1751-1761).

The promising results with bR stabilization led to investigating a more challenging system, the photosynthetic superassembly formed by the light harvesting I (LHI) and reaction center (RC) complexes from *Rhodobacter capsulatus* (Laible et al., *Biochemistry* 2003, 42, 1718-1730). This superassembly contains 30-40 protein molecules (five different components), and maintenance of native quaternary structure can be assessed via spectrophotometry. The LHI-RC superassembly was extracted from native membranes with 1.0 wt % DDM and purified with DDM at its CMC (0.009 wt %).

This preparation was diluted 20-fold with solutions containing TFA-1, TFA-2 or TFA-3, so that residual DDM was far below its CMC (0.0004 wt. %). The final TFA concentrations were 0.043 wt % (well over the CMC in each case). A control sample had DDM added to a total concentration of 0.049 wt % (all samples were CMC+0.04 wt %). FIG. 3b shows that LHI-RC superassembly solubilized with any of the TFAs was more stable over 20 days than was the superassembly solubilized by DDM. Controls involving other common biochemical detergents (lauryldimethylamine oxide or octyl-glucoside) showed rapid degradation of the superassembly (see Examples below).

Figure 4:
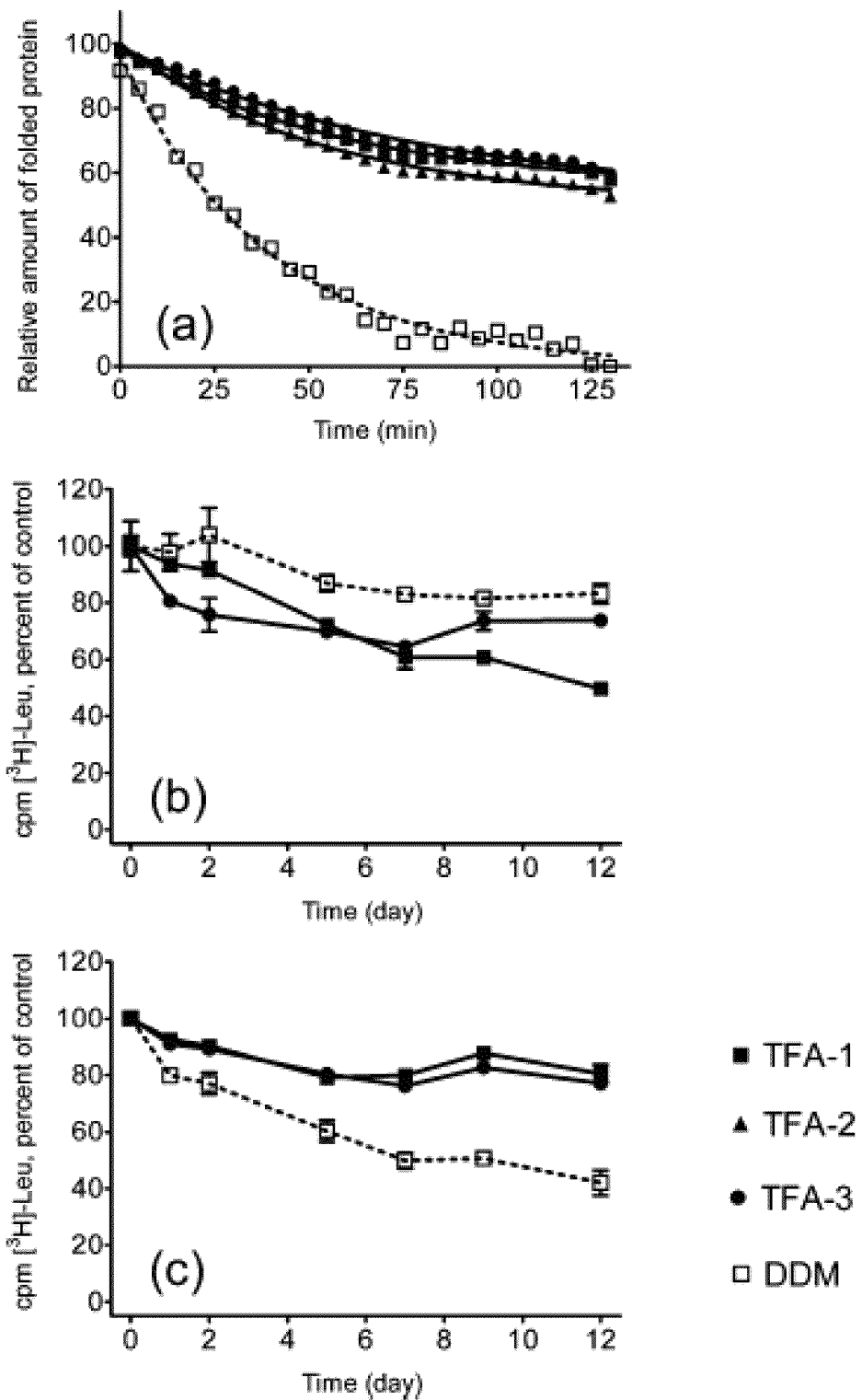
FIG. 4. Experimental assessment of the time-course changes in stability of solubilized Cyt bo₃ and activity of LeuT WT. (a) CPM assay for Cyt bo₃ was performed at 40° C. for 130 minutes using CMC+0.04 wt % amphiphile. LeuT WT was kept at room temperature for up to 12 days in the presence of CMC+0.04 wt % (b) or CMC+0.2 wt % (c) before determining binding activity by scintillation proximity assay (SPA).

Each membrane protein (such as bR) or membrane protein assembly (such as LHI-RC) has unique requirements for maintenance in a native-like state in aqueous solution; therefore, it is important to assess the capabilities of new amphiphiles in multiple systems, in order to establish the breadth of their utility. The analysis turned next to cytochrome $bo_3$ ubiquinol oxidase (Cyt $bo_3$), the structural stability of which was assessed at elevated temperature (40° C.) with a reactive probe, (N-[4-(7-diethylamino-4-methyl-3-coumarinyl)phenyl]maleimide) (CPM) (Hanson et al., *Structure* 2008, 16, 897-905). This maleimide derivative reacts with the thiol groups of sterically accessible Cys side chains. The coumarin moiety of CPM is internally quenched by the maleimide unit, but thiol reaction causes the unit to become fluorescent. CPM can therefore be used to detect thermally-induced protein unfolding, via an increase in fluorescence, if the protein contains Cys residues that are buried in the native state but accessible upon unfolding. Cyt $bo_3$ was initially extracted from the native membrane with DDM, and then diluted to generate solutions containing 0.043 wt % TFA-1, TFA-2 or TFA-3 (residual DDM=0.0008 wt %). A control sample had DDM added to a total concentration of 0.049 wt % (CMC+0.04 wt % for each amphiphile). FIG. 4a shows that TFA-solubilized Cyt $bo_3$ samples were more resistant to thermal denaturation than the DDM-solubilized control.

The wild type of bacterial leucine transporter (LeuT WT) was examined because the functional state of this membrane protein is readily assessed by using a scintillation proximity assay (SPA) (Quick et al., *Proc. Natl. Acad. Sci. USA* 2007, 104, 3603-3608) to monitor binding of radiolabelled leucine. LeuT was initially extracted with DDM and then diluted with amphiphile-containing solutions to generate final TFA concentrations of 0.04 wt % or 0.2 wt % (residual DDM=0.005 wt %). Control samples had 0.05 wt % or 0.2 wt % DDM (overall, the final concentrations were CMC+0.04 wt % or CMC+0.2 wt %). At the lower amphiphile concentrations, DDM was slightly better than the TFAs at maintaining LeuT WT function over 12 days (FIG. 4b), but the TFAs were clearly superior at the higher concentrations (FIG. 4c). TFA-1 and TFA-3 at the higher concentration matched DDM at the lower concentration in maintaining LeuT WT activity over the time period.

As a further test, the TFAs were examined for the ability to stabilize a GPCR, the human $\beta_2$ adrenergic receptor ($\beta_2AR$) (Rosenbaum et al., *Science* 2007, 318, 1266-1273). This assay employs a $\beta_2AR$-T4-lysozyme fusion protein ($\beta_2AR$-T4L) complexed to the inverse agonist carazolol. Stability was assessed by following the fluorescence emission maximum of carazolol, which shifts from 341 nm in the bound state to 356 nm in aqueous solution (i.e., after release upon $\beta_2AR$ denaturation). Monitoring the 341:356 nm peak intensity ratio upon heating yields cooperative denaturation data. However in this specific assay, the TFAs were slightly less effective than DDM.

In summary, a new class of molecules, "tandem facial amphiphiles" that contain two deoxycholate-derived subunits and that are sufficiently long to span a lipid bilayer, have been prepared and analyzed. These molecules can be easily prepared on a scale that would support biochemical research. One of the new amphiphiles, TFA-1, was shown to form small, discrete micelles in water (MW~13 kD). In contrast, DDM, a popular biochemical detergent, forms much larger micelles (MW~90 kD). Three TFAs have been rigorously evaluated for the ability to maintain intrinsic membrane proteins or protein assemblies in native-like forms in aqueous solution. In four of five also cases examined in detail, the TFAs proved to be comparable or superior to DDM for stabilizing the membrane protein.

Given the great variation in structure and physical properties among membrane proteins, no single amphiphile or amphiphile family will be maximally effective for every case. Because the TFAs manifest favorable solubilization/stabilization behavior with several diverse membrane protein systems, relative to widely used conventional detergents (DDM or OTG), and because this new amphiphile class can form small assemblies, the TFAs provide valuable tools for characterization of membrane proteins. An example of such tools can include, for example, high-resolution structural analysis (Privé, *Methods* 2007, 41, 388-397).

Example 3

Amphiphile Characterization

Calculation of the Length of the Hydrophobic Groups of the TFAs by Chem3D.

Figure 5:
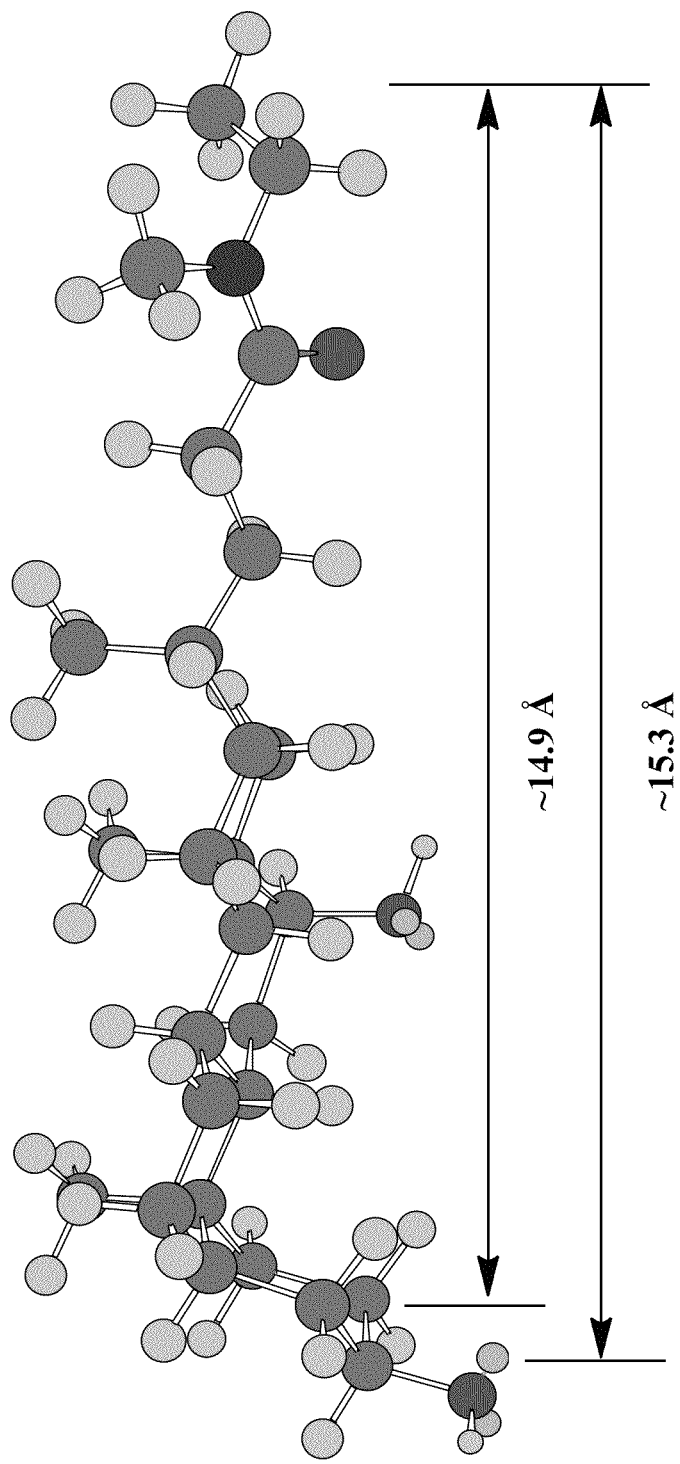
FIG. 5. Calculation of the length of the hydrophobic group common to the TFA amphiphiles was determined by measuring half the TFA chemical structure after MM2 energy minimization using Chem3D software (CambridgeSoft, Cambridge, Mass.).

The length of the hydrophobic group common to the TFA amphiphiles was determined by measuring half of the chemical structure (FIG. 5) after MM2 energy minimization using Chem3D software. The hydrophobic group adopts an extended conformation that is representative of conformations populated by TFA amphiphiles when they interact with hydrophobic patches of membrane proteins. This approach gave a total TFA amphiphile length estimate of approximately 29-31 Å, which corresponds to the length of the hydrophobic portion of a typical lipid bilayer (~30 Å).

Hydrodynamic Radii ($R_h$) Determination for TFAs and DDM Using Dynamic Light Scattering (DLS) Measurements.

Each TFA and DDM was dissolved in distilled, deionized (DI) water to obtain 1 mL of a solution containing 0.5 wt % amphiphile. Each solution was filtered through a 0.02 μm filter for DLS measurements. A 100-mW, 532-nm laser (Compass 315M-100, Coherent, Santa Clara, Calif.) illuminated a temperature-controlled glass cell at 25° C. that was filled with a refractive-index matching fluid (decahydronaphthalene, Fisher Scientific, Pittsburgh, Pa.). The scattered light was collected at an angle of 90° for about 30 minutes. $R_h$ values were determined using the integrated dynamics software that analyzes the time scale of the scattered light intensity fluctuations by an autocorrelation function. The autocorrelation functions (ACFs) were obtained using a BI-9000AT digital autocorrelator (Brookhaven Instruments, Holtsville, N.Y.). Measurements were repeated three times. The viscosity of pure water (0.89 cp at 25° C.) was used for all calculations, with the determination that the low detergent concentration (0.5 wt %) does not have a significant effect. $R_h$ values are expressed as mean±SD (n=3), as shown in Table 1 above.

Micelle Characterization of TFA-1 and DDM Using Triple Detector Analysis (TDA).

The on-line SEC triple detector array (Gatta et al., *Anal. Biochem.* 404, 21 (2010)) (Viscotek Corporation, a Malvern Company) used for detergent analysis is composed of 1) a 660 nm differential refractometer for quantifying the concentration C (mg/mL) for all molecules according to their specific refractive index increment do/dc (mL/g) using Snell's Law of Refraction (RI signal=$K_{RI}$*C*(dn/dc)/$RI_{Sol}$), 2), a single right angle 90° static light scattering (RALS) detector for measuring the average mass M (Da) according to the Raleigh Light Scattering Equation for small molecules ($LS_{90}°$ signal=$M_{avg}$*$RI_{sol}^2$*C*$(dn/dc)^2)/K_{Ls}$*$K_{opt}$, where $K_{opt}$=4*$\pi^2/(\lambda^4$*$N_A$), and 3) an absolute differential viscometer (Haney, *J. Appl. Polym. Sci.* 30, 3023 (1985)) for measuring differential pressure (DP) and calculating intrinsic viscosity (IV; dL/g) according to Newtonian Viscosity (liquid layers) applied to tubes using Poiseulle's Law (DP signal=IV*C) and for calculating the radius of hydration Rh (nm) according to Einstein's volume of hydration equation for hard spheres ($R_h$=[(3/10$\pi$)*IV*M/$N_A$]$^{1/3}$).

The IV represents molecular shape and for proteins it can vary from 0.017 dl/g for globular shapes to 0.355 dl/g for elongated shapes to 0.499 dl/g for complete denaturation (Scheraga and Mandelkern, *J. Chem. Phys.* 75, 179-184 (1953); Dutta et al., *J. Chromatogr.* 536, 113-121 (1991); Chenal et al., *J. Biol. Chem.* 16, 284(3), 1781-1789 (2009)). The chromatography pump, injector, SEC column (0.75×60 cm TSK G3000 plus guard column), and TDArray are placed in a 4° C. cold box, while the buffer (degassed for more than 1 hr with stir prior use) is at room temperature (RT) to allow it to be run through a RT on-line degasser, which then runs though 3 ft of 4° C. stainless steel tubing before entering the SEC pump, injector and column. The extensive degassing insures an accurate DP measurement. With this configuration, the temperature at the detectors is 6° C. TDA buffer was 20 mM Hepes, 150 mM NaCl, pH 7.3 and either 0.1 mM TFA-1 or 1 mM DDM. The refractive index of the solvent $RI_{Sol}$ was measured at 10° C. using an Anton Paar Abbemat temperature controlled refractometer at 589.2 nm. Triple detection data at every 5 Hz data point throughout the complete SEC peak were used for all analysis.

Figure 6:
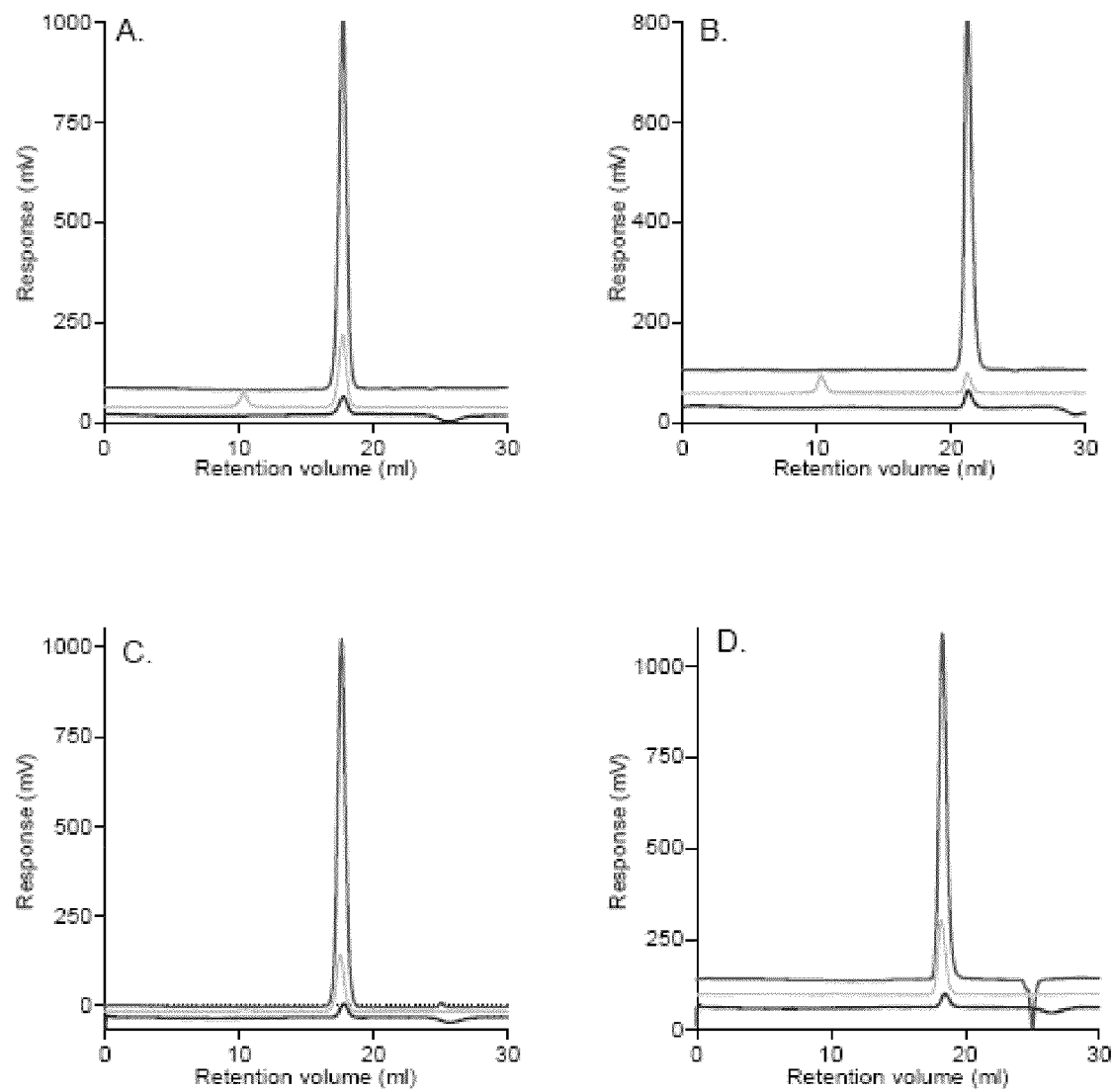
FIG. 6. Examples of TDA SEC profiles (TDAgrams) of (A) 0.68 mg Ovalbumin and (B) 0.53 mg TFA-1 in TFA buffer and (C) 0.60 mg Ovalbumin and (D) 0.8 mg DDM in DDM buffer.

For calibration, the detector response factors $K_{RI}$ and $K_{LS}$ were measured using Ovalbumin Fraction VII (Sigma). Prior to calibration, ovalbumin was first purified by SEC (280 nm detection) at 4° C. to remove small populations of dimers and aggregates, and to insure Gaussian detector peaks for TDA calibration. Ovalbumin was solubilized at 26 mg/mL in TDA buffer at 4° C. for 10 min and clarified by centrifugation (10 min 15,000×g); collecting the top 30% of the SEC elution peak from 500 μL injections yielded monodisperse ovalbumin at 5-7 mg/mL. Ovalbumin mass was 44.3 kDa (Sigma Product Information sheet and references therein) with a 0.701 $dA_{280nm}$/dc (Pace et al., *Prot. Sci.* 4(11), 2411-2423 (1995)) and 0.187 dn/dc (Maezawa et al., *Biochem. Biophys. Acta* 747, 291-297 (1983); Hayashi et al., *Methods Enzymol.* 172, 514-528 (1989)). The absolute error of the detector response factors from 4 measurements for each detergent was ≤0.1% for TFA-1 buffer and ≤0.2% for DDM buffer. Examples of TDA SEC profiles (TDAgrams) are shown in FIG. 6.

Figure 7:
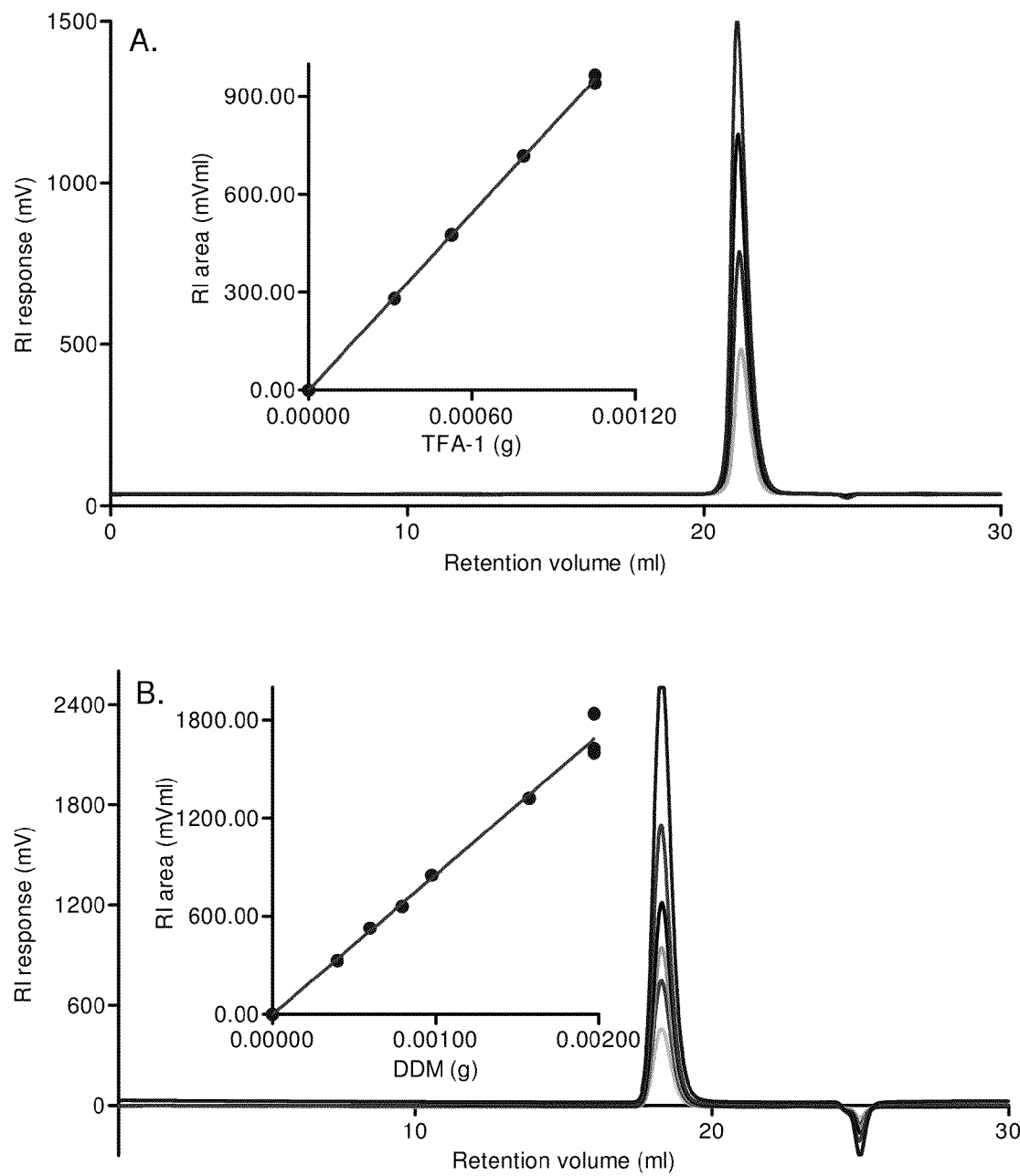
FIG. 7. Measuring detergent dn/dc using TDA. Overlay of the RI traces used to calculate dn/dc (inset) from (A) 7 different TFA-1 injections (0 to 1.05 mg; 4 shown) and (B) 10 different DDM injections (0 to 1.97 mg; 6 shown).
Figure 8:
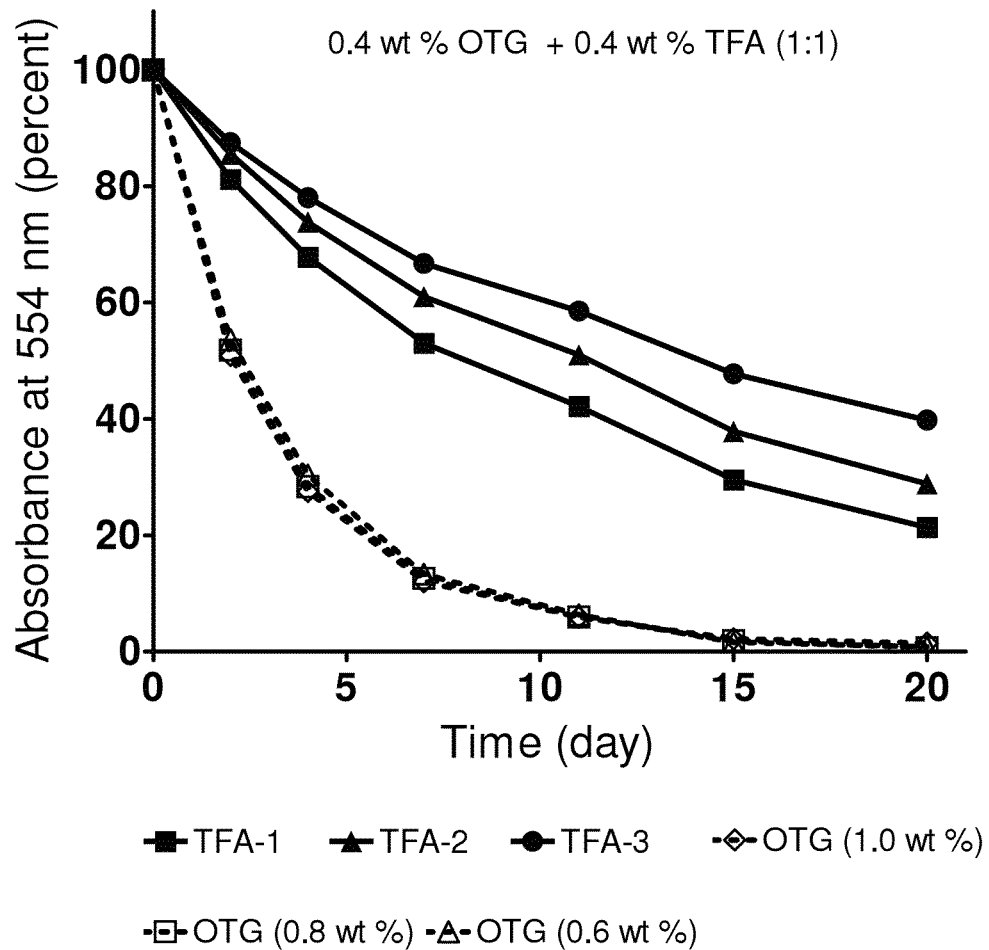
FIG. 8. Time course of bR stability evaluated at room temperature. OTG was mixed with each TFA in a ratio of 1:1 or alone (0.6 wt %, 0.8 wt %, or 1.0 wt %). Absorbance at 554 nm was followed for the stability evaluation of the protein.

Measuring detergent dn/dc using TDA provided the data illustrated in FIG. 7. Overlay of the RI traces used to calculate dn/dc (inset) from 7 different (0 to 1.05 mg; 4 shown) TFA-1 injections (A) and 10 different (0 to 1.97 mg; 6 shown) DDM injections (B). RI data and analysis used to measure detergent dn/dc are shown in FIG. 8.

Protein Stability Evaluation:

Stabilization Assay For Bacteriorhodopsin (bR).

The general procedure was followed according to the reported protocol of Bazzacco et al. (*Biomacromolecules* 10, 3317-3326 (2009)). Frozen aliquots of purple membranes containing bR at 184 μM were thawed and solubilized by incubation with octylthioglucoside (OTG) for 24 hr at 4° C. in a dark room. For the solubilization, OTG (CMC=0.28 wt %) was used at 2.0 wt % in 10 mM sodium phosphate (pH 6.9). Subsequently the solubilized material was separated from the membrane debris in an ultracentrifuge at 200,000×g at 4° C. for 20 min. The supernatant from the spin was collected and transferred into individual TFA solutions to give final detergent/amphiphile concentration of OTG:TFA=0.4 wt %:0.4 wt % (1:1) or 0.2 wt %:0.8 wt % (1:4). BR stability in each TFA solutions was monitored by measuring absorbance at 554 nm for 20 days.

Stabilization Assay for *R. capsulatus* Superassembly.

The general procedure was followed according to the reported protocol (Chae et al., *ChemBioChem* 9, 1706-1709 (2008)). Briefly, specialized photosynthetic membranes were prepared from an engineered strain of *Rhodobacter* (*R.*) *capsulatus*, U43[pUHTM86Bg1], lacking the LHII light-harvesting complex and used as the starting material. The solubilization and purification of LHI-RC superassembly were started by thawing, homogenizing, and equilibrating frozen aliquots of *R. capsulatus* membranes at 32° C. for 30 min. Addition of DDM at 1 wt % concentration to 1 mL aliquots of the membranes was followed by incubation of the membrane samples at 32° C. for 30 min. Subsequently, the solubilized material was collected and transferred into a new microcentrifuge tube containing Ni-NTA resin (Qiagen, Inc.; Valencia, Calif.; pre-equilibrated and stored in an equal volume of buffer containing 10 mM Tris, pH 7.8, and 100 mM NaCl) after an ultracentrifuge at 315,000×g at 4° C. for 30 min. The tubes were then incubated and inverted for 1 hour at 4° C. for binding.

Resin-retaining spin columns (e.g., emptied His Spin-Trap™ columns; GE Healthcare) were inserted into a 2 mL microcentrifuge tube and the samples were then loaded onto the column. Samples were washed twice with 0.5 mL of binding buffer (a pH 7.8 Tris solution containing DDM at 1×CMC). The protein was collected by eluting with two 0.25 mL elution buffer aliquots (this buffer was identical to binding buffer with the addition to 1 M of imidazole; the pH of each solution was checked and readjusted to pH=7.8). Small aliquots (0.05 mL) of the purified protein solutions were transferred to 0.95 mL individual amphiphiles/detergents solutions at the designated concentrations (CMC+0.04 wt %, CMC+0.2 wt %, CMC+0.5 wt % and CMC+1.0 wt %) and incubated at room temperature.

Figure 9:
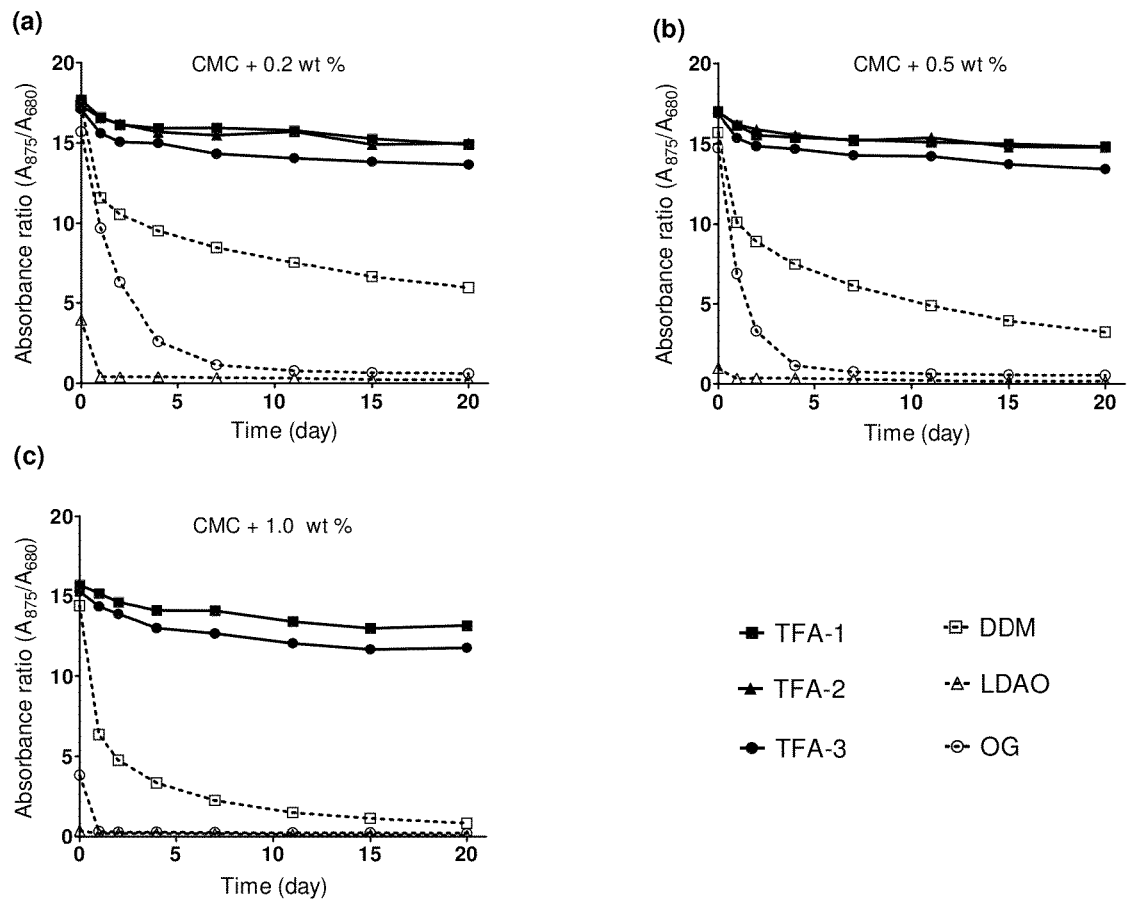
FIG. 9. Time course of stability of R. capsulatus superassembly was evaluated at room temperature. Each TFA was used at three different concentrations (CMC+0.2 wt %, CMC+0.5 wt %, or CMC+1.0 wt %). Absorbance ratio ($A_{875}/A_{680}$) was followed for the stability evaluation of the membrane protein.
Figure 10:
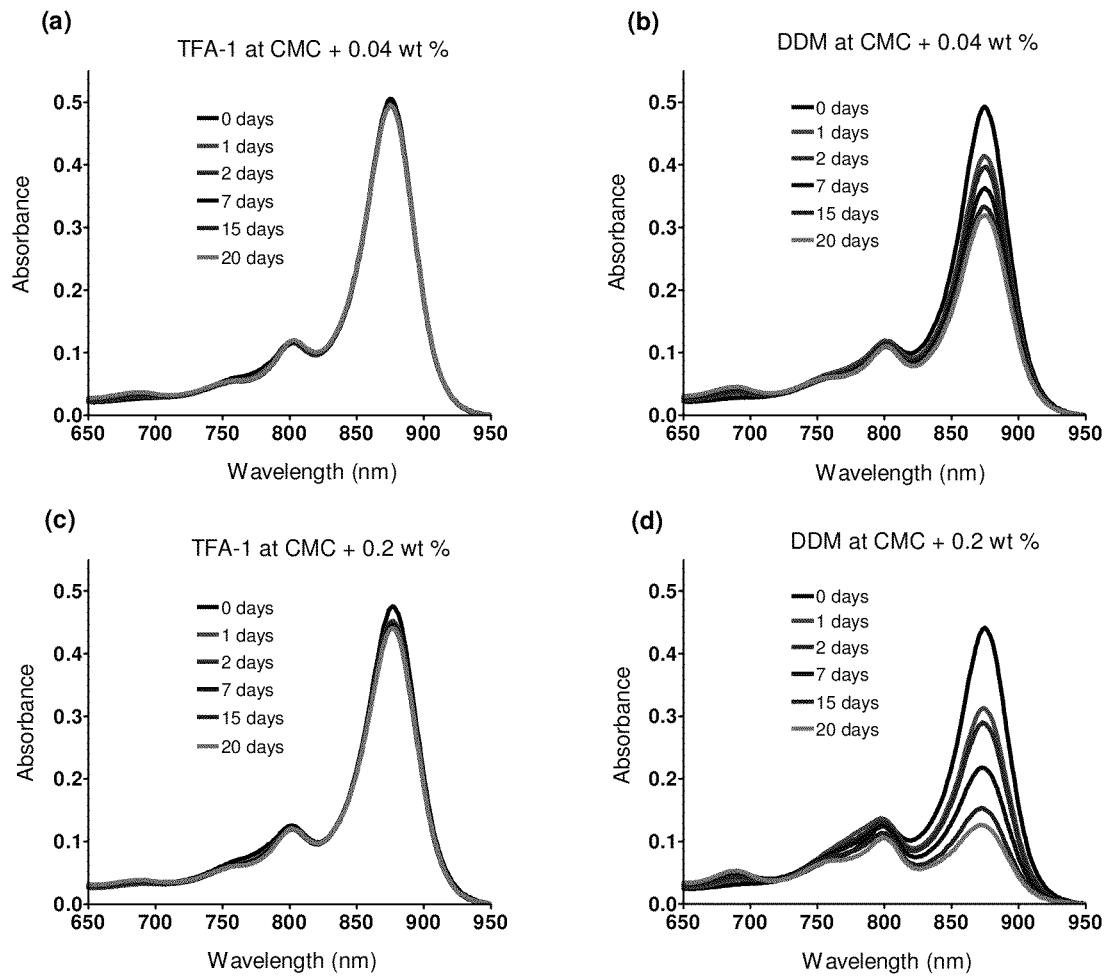
FIG. 10. Absorbance spectrum of *R. capsulatus* superassembly in TFA-1 (a,c) and DDM (b,d) at room temperature. Each agent was used at two concentrations (CMC+0.04 wt % and CMC+0.2 wt %).

UV-Vis spectra of these solutions were measured in regular intervals. FIG. 9 illustrates the time course of stability of *R. capsulatus* superassembly, evaluated at room temperature. Each TFA was used at three different concentrations (CMC+0.2 wt %, CMC+0.5 wt %, or CMC+1.0 wt %). Absorbance ratio ($A_{875}/A_{680}$) was followed for the stability evaluation of the membrane protein. Degradation of the material was monitored with the 875 nm/680 nm absorbance ratio, which decreased with time and sample integrity as the dominant 875 nm absorption of intact LHI disappeared and a 680 nm band, indicating the presence of unbound, oxidized cofactors, appeared. FIG. 10 illustrates the absorbance spectrum of *R. capsulatus* superassembly in TFA-1 (a,c) and DDM (b,d) at room temperature (~23° C.). Each agent was used at two concentrations (CMC+0.04 wt % and CMC+0.2 wt %).

Thermal Stability Assay for CytBO3.

The thermal stability assay method was performed as described (Alexandrov et al., *Structure* 16, 351-359 (2008)) with the following minor modifications. CPM (Invitrogen) dye aliquots, stored in DMSO (Sigma), were diluted in dye buffer [20 mM Tris (pH 7.5), 150 mM NaCl, 0.03% DDM, 5 mM EDTA]. All the detergent/amphiphiles were used at CMC+0.04 wt % in test buffer [20 mM Tris (pH 7.5), 150 mM NaCl]. Greiner 96-well plates were used, and the volume of selected buffer solutions was 150 μL. The test protein (10 mg/mL) was diluted in the assay buffer solutions (1:150) in Greiner 96-well plates, and 3 μL of diluted CPM dye was added to each test condition. The reaction was monitored for 130 mM at a fixed temperature of 40° C. using a microplate spectrofluorometer set at an excitation wavelength of 387 nm and an emission wavelength of 463 nm. Readings were taken every 5 min after automatic agitation of the plate. Relative maximum fluorescence count was used to calculate percentage of relative folded protein remaining after 130 minutes at 40° C. Relative unfolding profiles of proteins were plotted against time using GraphPad Prism using the one-phase decay equation.

LeuT Solubility And Functionality Assay.

Figure 11:
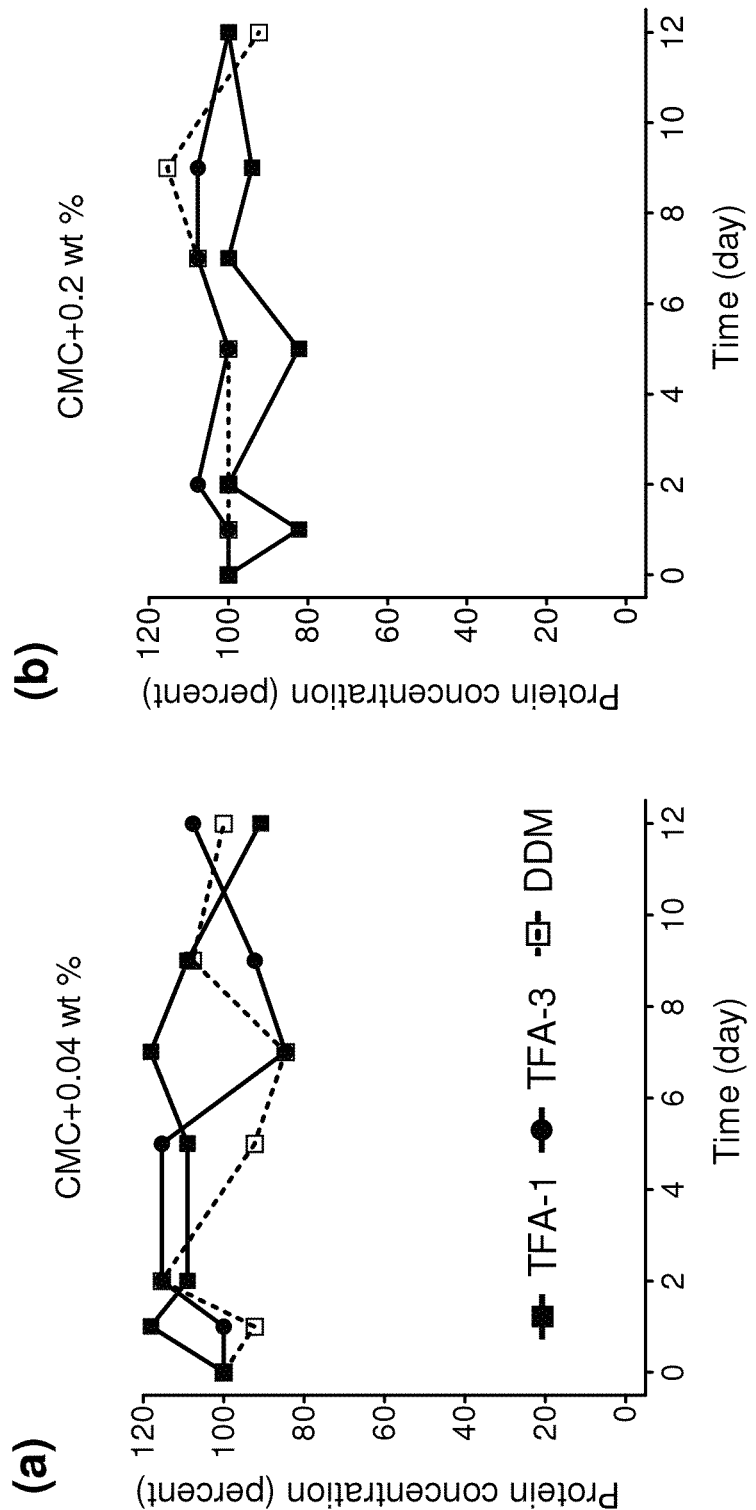
FIG. 11. Long-term solubility of LeuT WT incubated in the presence of TFA-1, TFA-3, and DDM at (a) CMC+0.04 wt % or (b) CMC+0.2 wt % at room temperature (~23° C.).

The wild type of the leucine transporter (LeuT WT) from *Aquifex aeolicus* was expressed in *Escherichia coli* essentially as described by Deckert et al. (*Nature* 392, 353-358 (1998)). The pET16b-LeuT WT-8His plasmid was kindly provided by Dr. Eric Gouaux, Vollum Institute, Portland Oreg. LeuT WT was extracted from isolated bacterial membranes solubilized with 1% DDM, bound to $Ni^{2+}$-affinity Chelating Sepharose Fast Flow resin (GE Healthcare, USA), and eluted in buffer consisted of 20 mM Tris-HCl (pH 8.0), 1 mM NaCl, 199 mM KCl, 0.05% DDM and 300 mM imidazole. Subsequently, selected LeuT WT fractions were pooled, aliquoted and diluted in the above-mentioned buffer without DDM, but containing TFA-1 or TFA-3 in a final concentration of CMC+0.04 wt % or CMC+0.2 wt %, respectively. Alternatively, as a control, DDM was used at the above-mentioned final concentrations. After incubation at room temperature, at the indicated time points, samples were centrifuged and the protein concentration was determined by absorbance measurements at 280 nm. Concomitantly, [$^3$H]-Leu binding was determined using scintillation proximity assay (SPA) (Quick and Javitch, *Proc. Natl. Acad. Sci. USA* 104, 3603-3608 (2007)), with the reaction mixture consisted of 5 μL from the respective samples, 33.3 nM [$^3$H]-Leu (PerkinElmer, USA) and copper chelate (His-Tag) YSi beads (GE Healthcare). NaCl and the tested compounds at the above-mentioned concentrations. For each time point, double determination of [$^3$H]-Leu binding was performed using MicroBeta liquid scintillation counter (PerkinElmer). Normalized results are expressed as mean±SEM (n=2), as illustrated in FIG. 11 (long-term solubility of LeuT WT incubated in the presence of TFA-1, TFA-3, and DDM at (a) CMC+0.04 wt % or (b) CMC+0.2 wt % at room temperature).

Temperature Ramp Stability Assay for $β_2$AR-T4L.

Sf9 insect cell cultures expressing baculovirus encoded $β_2$AR-T4L were solubilized and purified in DDM as previously described (Rosenbaum et al., *Nature* 318, 1266-1273 (2007)). Briefly, the receptor was purified by M1 FLAG antibody (Sigma) chromatography followed by alprenolol-Sepharose affinity chromatography. The receptor was immobilized in a second M1 chromatography step and washed extensively in buffer (0.1% DDM, 100 mM NaCl, 20 mM HEPES, pH 7.5) containing 30 μM carazolol to exchange bound alprenolol. The eluted carazolol-bound receptor was dialyzed against buffer containing 1 μM carazolol and spin concentrated to 7 mg/ml (≈140 μM) using a 100 kDa molecular weight cut-off Vivaspin (Vivascience) concentrator. For stability measurements the carazolol-bound $β_2$AR-T4L was diluted below the CMC for DDM by adding 3 μL of the concentrated receptor in a quartz cuvette containing 600 μL buffer (100 mM NaCl, 20 mM HEPES, pH 7.5) with TFA-1 and TFA-3. The cuvette was placed in a Spex FluoroMax-3 spectrofluorometer (Jobin Yvon Inc.) under Peltier temperature control. Fluorescence emission from carazolol was obtained following 5 min incubations from 25 to 85° C. in twelve continuous 5° C. increments. Emission was obtained from 335 to 400 nm with excitation set at 325 nm using an integration time of 0.3 s $nm^{-1}$ and a 1 nm band-pass for both excitation and emission. The 341:356 nm peak ratio was calculated using Microsoft Excel and graphed using GraphPad Prism software.

Example 4

Examples of Amphiphiles

Several amphiphiles (TFA 1a-10a) were prepared and evaluated for their water solubility and critical micelle concentration (CMC). Several of the TFAs were found to be water soluble and suitable for use in manipulating membrane proteins. Examples of these TFAs include compounds of Formula VI:

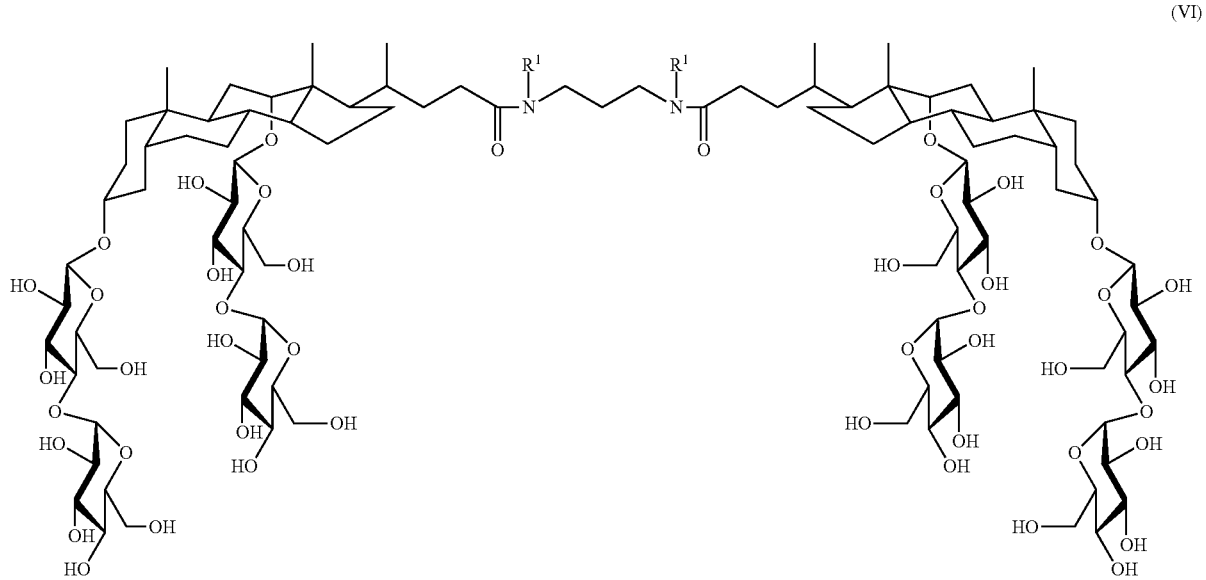

(VI)

where $R^1$ is as follows:
TFA-3a: $R^1$=H;
TFA-4a: $R^1$=CH$_3$;
TFA-7a: $R^1$=CH$_2$CH$_3$;
TFA-8a: $R^1$=CH$_2$(CH$_3$)$_2$;
TFA-9a: $R^1$=(CH$_2$)$_3$CH$_3$;
TFA-10a: $R^1$=(CH$_2$)$_4$CH$_3$.

With very small changes in the chemical structure of the amphiphiles, some TFAs were found to be generally water-insoluble. These TFAs can be used to prepare hydrogels, which can be used tissue engineering or drug delivery applications. Examples of the generally water-insoluble TFAs include compounds of Formula XX:

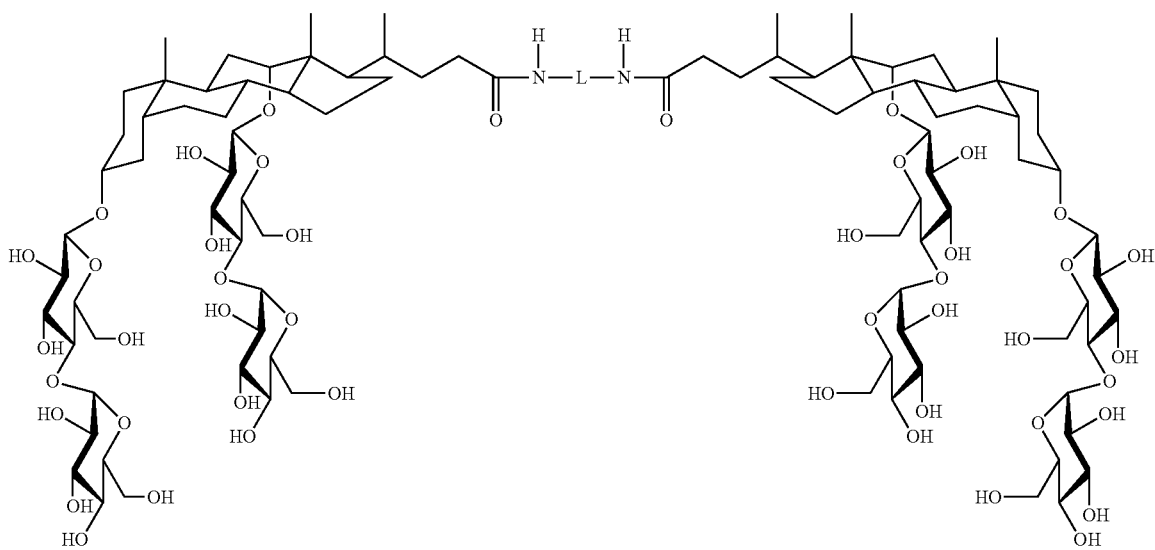

(XX)

where L is as follows:
TFA-1a: L=(CH$_2$)$_2$;
TFA-2a: L=(CH$_2$)$_4$;
TFA-5a: L=cyclohexyl;
TFA-6a: L=p-xylyl.

Analysis of these TFAs for their CMC values provided the data in Table 3. While TFA-2a, TFA-5a, and TFA-6a were insoluble under the conditions evaluated, a CMC was obtainable for poorly water soluble TFA-1a. While soluble, TFA-3a was also able to form a hydrogel in water.

TABLE 3

CMC Values of various TFAs.

| Detergent | M.W. | CMC (mM) | CMC (wt. %) |
|---|---|---|---|
| TFA-1a | 2120.4 | 0.06 | 0.013 |
| TFA-2a | 2148.4 | — | — |
| TFA-3a | 2134.4 | 0.06 | 0.0128 |
| TFA-4a | 2148.4 | 0.014 | 0.0030 |
| TFA-5a | 2160.4 | — | — |
| TFA-6a | 2182.4 | — | — |
| TFA-7a | 2176.5 | 0.013 | 0.0028 |
| TFA-8a | 2204.5 | 0.015 | 0.0033 |
| TFA-9a | 2232.6 | 0.01 | 0.0022 |
| TFA-10a | 2260.6 | 0.004 | 0.0009 |

As described above, TFAs corresponding to TFA-1a-10a can be prepared where the maltose moiety is exchanged for any monosaccharide, disaccharide, or trisaccharide, to provide other compounds of the invention, depending on the desired structure and properties.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method of solubilizing or stabilizing a membrane protein comprising contacting a membrane protein with an effective amount of a plurality of compounds, in an aqueous solution, and optionally heating the protein and the compounds, thereby forming a solubilized or stabilized aggregation of the compounds and the membrane protein, wherein the plurality of compounds comprises compounds of Formula I:

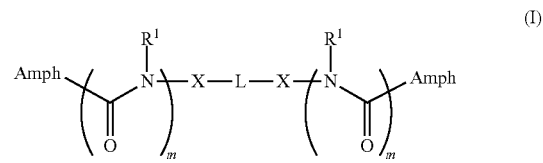

(I)

wherein
L is (C$_5$-C$_8$)cycloalkyl; phenyl optionally by 1-4 (C$_1$-C$_4$) alkyl; —C(R$^x$)$_2$—; or —CH$_2$—C(R$^x$)$_2$—CH$_2$—; where each R$^x$ is independently OH, or —CH$_2$O-Sac;
each X is independently O, S, NH, triazole; or a direct bond;
each m is 0 or 1;

each $R^1$ is independently H or $(C_1-C_{20})$alkyl; and
each Amph is independently a moiety of Formula A:

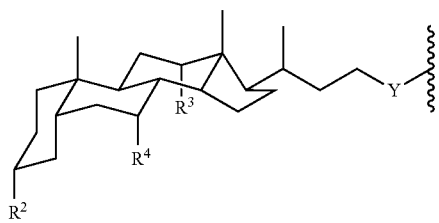

(A)

wherein
Y is $CH_2$ or a direct bond;
each $R^2$, $R^3$, and $R^4$ is independently H, OH, or O-Sac; and
each Sac is independently a monosaccharide, disaccharide, or trisaccharide;
wherein each of the compounds has at least 4 Sac groups.

2. The method of claim 1 wherein the aggregation of the compounds is in the form of a micelle.

3. The method of claim 1 wherein each $R^1$ is $(C_1-C_{20})$alkyl.

4. The method of claim 1 wherein Y is a direct bond.

5. The method of claim 1 wherein at least two of $R^2$, $R^3$ and $R^4$ are O-Sac and each Sac is a disaccharide.

6. The method claim 1 wherein the plurality of compounds comprises a compound of Formula III:

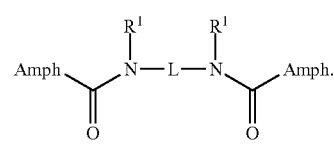

(III)

7. The method claim 1 wherein the plurality of compounds comprises a compound of Formula XII:

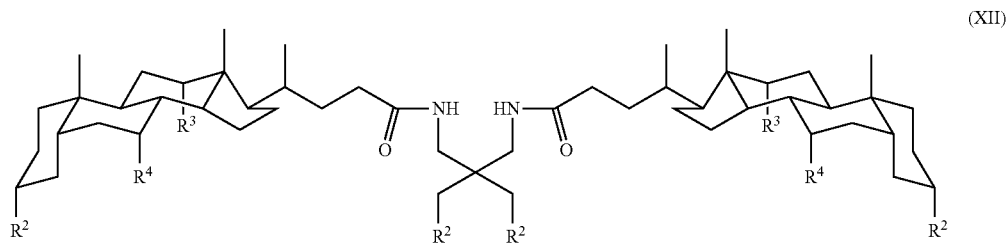

(XII)

where each $R^2$ is independently an oxygen-linked monosaccharide, disaccharide, or trisaccharide.

8. The method claim 7 wherein the plurality of compounds comprises:

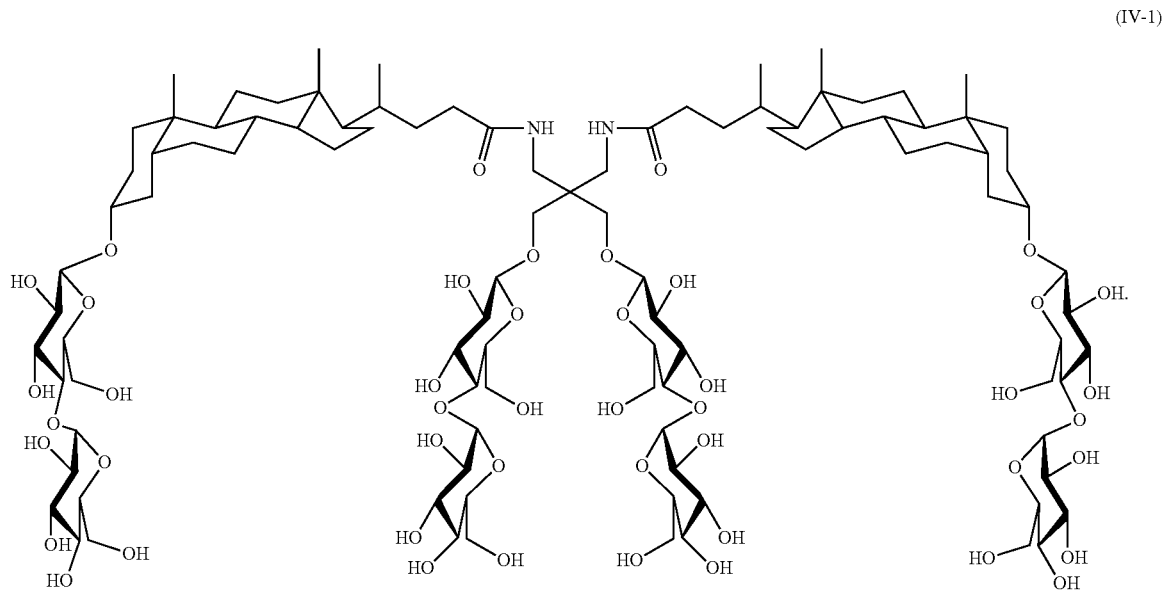

(IV-1)

9. The method claim 1 wherein the plurality of compounds comprises a compound of Formula XIII:
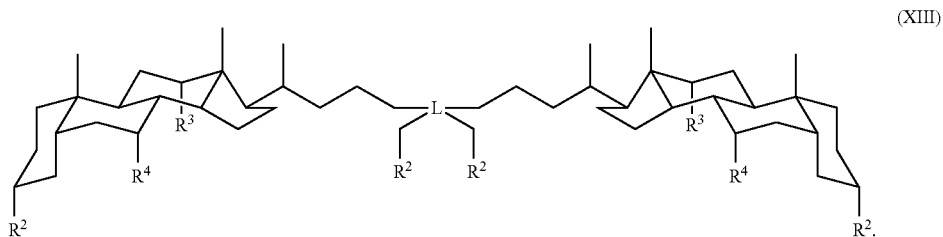
(XIII)
10. The method claim 9 wherein the plurality of compounds comprises:
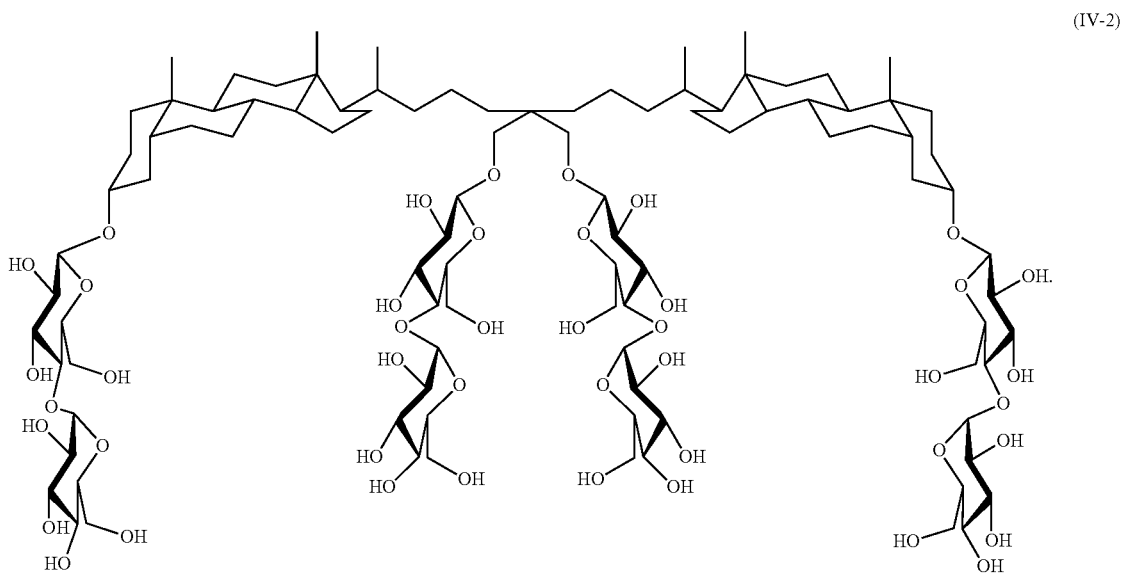
(IV-2)
11. The method claim 1 wherein the plurality of compounds comprises a compound of Formula XIV:
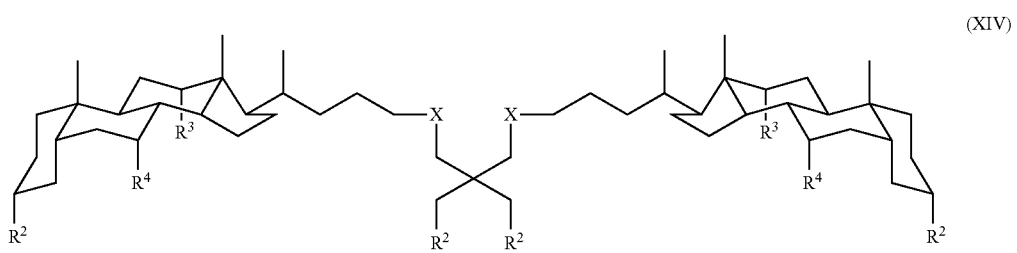
(XIV)
where each $R^2$ is independently a monosaccharide, disaccharide, or trisaccharide.

12. The method claim 11 wherein the plurality of compounds comprises:

(IV-3)

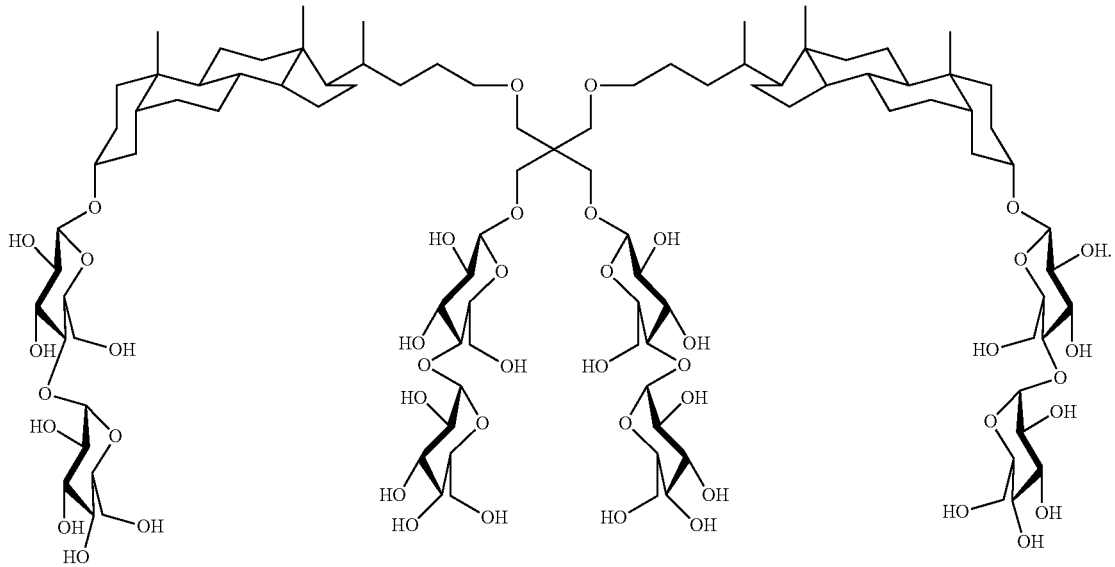

13. A method of solubilizing or stabilizing a membrane protein comprising contacting a membrane protein with an effective amount of a plurality of compounds, in an aqueous solution, and optionally heating the protein and the compounds, thereby forming a solubilized or stabilized aggregation of the compounds and the membrane protein, wherein the plurality of compounds comprises compounds of Formula I:

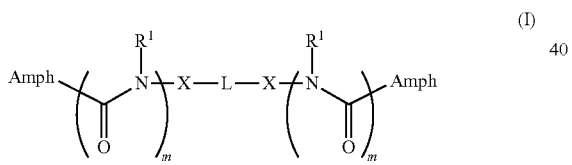

(I)

wherein
L is $(C_5-C_8)$cycloalkyl; phenyl optionally substituted by 1-4 $(C_1-C_4)$alkyl; —$(CH_2)_n$— where n is 1, 2, or 4-10; —$C(R^x)_2$—; or —$CH_2$—$C(R^x)_2$—$CH_2$—; where each IV is independently OH, or —$CH_2$O-Sac;
each X is independently O, S, NH, triazole; or a direct bond;
each m is 0;
each $R^1$ is independently H or $(C_1-C_{20})$alkyl; and
each Amph is independently a moiety of Formula A:

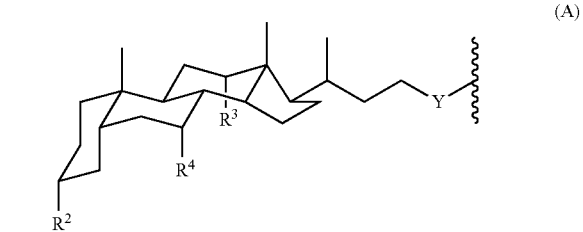

(A)

wherein
Y is $CH_2$ or a direct bond;
each $R^2$, $R^3$, and $R^4$ is independently H, OH, or O-Sac; and
each Sac is independently a monosaccharide, disaccharide, or trisaccharide;
wherein each of the compounds has at least 4 Sac groups.

14. The method of claim 13 wherein the aggregation of the compounds is in the form of a micelle.

15. The method of claim 13 wherein Y is a direct bond.

16. The method of claim 13 wherein at least two of $R^2$, $R^3$ and $R^4$ are O-Sac and each Sac is a disaccharide.

17. The method claim 13 wherein the plurality of compounds comprises a compound of Formula XIII:

(XIII)

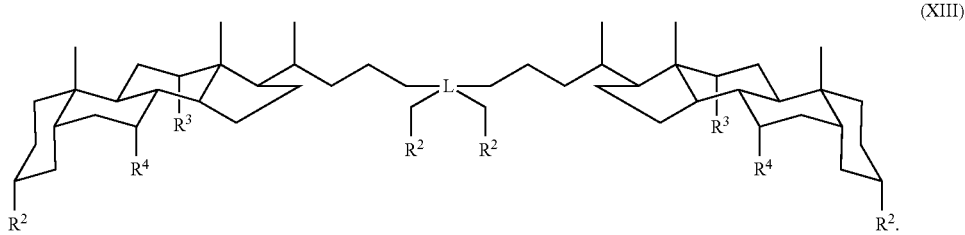

18. The method claim 17 wherein the plurality of compounds comprises:
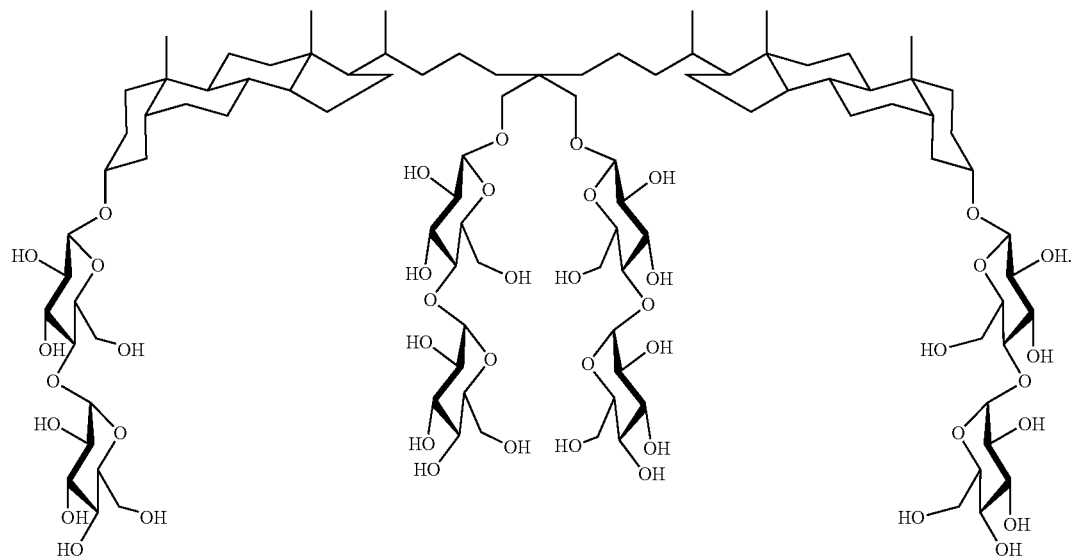
(IV-2)
19. The method claim 13 wherein the plurality of compounds comprises a compound of Formula XIV:
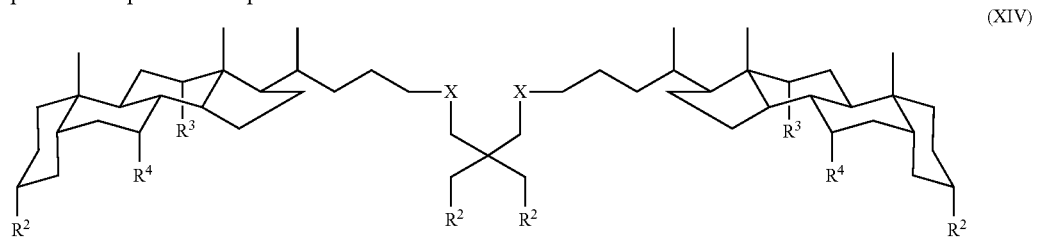
(XIV)
where each $R^2$ is independently a monosaccharide, disaccharide, or trisaccharide.
20. The method claim 19 wherein the plurality of compounds comprises:
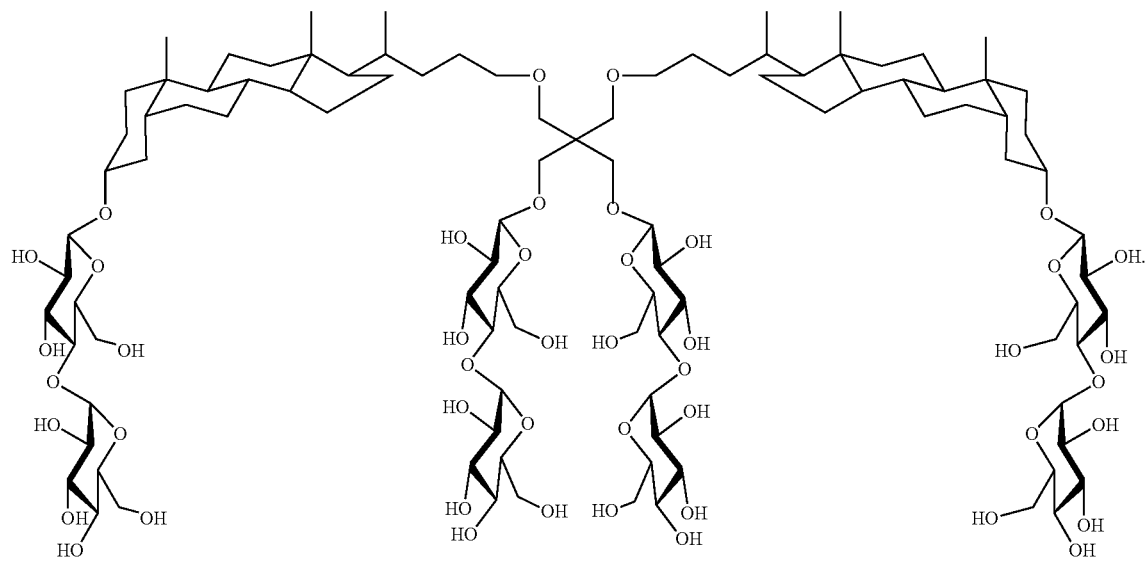
(IV-3)
* * * * *

UNITED STATES PATENT AND TRADEMARK OFFICE
CERTIFICATE OF CORRECTION

| | | |
|---|---|---|
| PATENT NO. | : 8,815,263 B2 | Page 1 of 1 |
| APPLICATION NO. | : 13/669198 | |
| DATED | : August 26, 2014 | |
| INVENTOR(S) | : Gellman et al. | |

It is certified that error appears in the above-identified patent and that said Letters Patent is hereby corrected as shown below:

In the Claims

Claim 1: Column 38, Line 62 should read: "L is...phenyl optionally substituted by 1-4..."

Claim 13: Column 43, Line 51 should read: "$R^x$ is independently..."

Signed and Sealed this
Thirteenth Day of January, 2015

Michelle K. Lee
*Deputy Director of the United States Patent and Trademark Office*